(12) United States Patent
Smet et al.

(10) Patent No.: US 9,155,666 B2
(45) Date of Patent: Oct. 13, 2015

(54) PRESS AND METHOD FOR PRODUCINIG ABSORBENT ARTICLE

(75) Inventors: Steven Smet, Zele (BE); Andreas Matthes, Grosspostwitz, DE (US)

(73) Assignee: ONTEX HIGIENEARTIKEL DEUTSCHLAND GMBH, Grosspostwitz (DE)

( * ) Notice: Subject to any disclaimer, the term of this patent is extended or adjusted under 35 U.S.C. 154(b) by 474 days.

(21) Appl. No.: 13/809,017

(22) PCT Filed: Jul. 6, 2011

(86) PCT No.: PCT/EP2011/061435
§ 371 (c)(1),
(2), (4) Date: Jan. 8, 2013

(87) PCT Pub. No.: WO2012/004315
PCT Pub. Date: Jan. 12, 2012

(65) Prior Publication Data
US 2013/0110074 A1    May 2, 2013

(30) Foreign Application Priority Data
Jul. 9, 2010 (EP) .................................... 10169005

(51) Int. Cl.
*A61F 13/20* (2006.01)
*B30B 7/04* (2006.01)

(52) U.S. Cl.
CPC ......... *A61F 13/2088* (2013.01); *A61F 13/2051* (2013.01); *A61F 13/2054* (2013.01); *A61F 13/2085* (2013.01); *B30B 7/04* (2013.01)

(58) Field of Classification Search
CPC .................. A61F 13/20–13/2097; B30B 7/04
See application file for complete search history.

(56) References Cited

U.S. PATENT DOCUMENTS 435,491 A    9/1890 Fredigké
1,731,665 A  10/1929 Huebsch
(Continued)

FOREIGN PATENT DOCUMENTS

AU    2006263937    1/2007
DE    3 934 153     4/1991
(Continued)

OTHER PUBLICATIONS

International Search Report dated Aug. 9, 2011 issued to priority international application No. PCT/EP2011/061435.
(Continued)

*Primary Examiner* — Lee D Wilson
*Assistant Examiner* — Tyrone V Hall, Jr.
(74) *Attorney, Agent, or Firm* — Knobbe, Martens, Olson & Bear, LLP

(57) ABSTRACT

The present invention relates to a press (100) for manufacturing a tampon, comprising at least three press jaws (6) arranged in a star around a central longitudinal press axis (4) forming a press opening (2), whereby there is provided on a single or separate adjacent press jaws (6): —a penetrating segment, PSLG, (13) configured to penetrate the absorbing material with a longitudinal groove, and —penetrating segments, PSSG, (11) configured to penetrate the absorbing material with a plurality of side grooves that are arranged in the longitudinal direction, wherein the press is configured to: a) load a cylindrical blank (200) in the press opening (2), b) move the press jaws (6) to a closed position to press the cylindrical blank (200) so forming a preform (210), c) move the press jaws (6) to a holding position between the closed position and open position, so that the preform can be removed, d) remove the preform while the jaws (6) are in the holding position, and e) move the press jaws (6) to the open position for loading of a subsequent cylindrical blank. It further relates to a method for manufacture of the tampon.

16 Claims, 11 Drawing Sheets

(56) References Cited

U.S. PATENT DOCUMENTS

| | | | |
|---|---|---|---|
| 1,941,717 A | 1/1934 | Rabell | |
| 1,964,911 A | 7/1934 | Haas | |
| 2,263,909 A | 11/1941 | Webb | |
| 2,355,628 A | 8/1944 | Calhoun | |
| 2,425,004 A * | 8/1947 | Rabell | 28/118 |
| 2,444,528 A | 7/1948 | Popper et al. | |
| 2,499,414 A | 3/1950 | Rabell | |
| 2,652,056 A | 9/1953 | Lay | |
| 2,706,986 A | 4/1955 | Carrier | |
| 2,798,260 A * | 7/1957 | Niepmann et al. | 28/119 |
| 2,965,101 A | 12/1960 | Schirmer et al. | |
| 3,011,495 A | 12/1961 | Brecht | |
| 3,013,558 A | 12/1961 | Curl | |
| 3,101,713 A | 8/1963 | Sargent | |
| 3,138,159 A | 6/1964 | Schmidt | |
| 3,148,680 A | 9/1964 | Roberts et al. | |
| 3,196,873 A | 7/1965 | Beltzinger et al. | |
| 3,397,695 A | 8/1968 | Voss | |
| 3,431,909 A | 3/1969 | Krusko | |
| 3,610,243 A | 10/1971 | Jones, Sr. | |
| 3,643,661 A | 2/1972 | Crockford | |
| 3,696,812 A | 10/1972 | Jaycox | |
| 3,717,149 A | 2/1973 | Morane | |
| 3,834,389 A | 9/1974 | Dulle | |
| 3,981,305 A | 9/1976 | Ring | |
| 4,077,409 A | 3/1978 | Murray et al. | |
| 4,109,354 A * | 8/1978 | Ronc | 28/119 |
| 4,175,561 A * | 11/1979 | Hirschman | 604/385.17 |
| 4,276,881 A | 7/1981 | Lilaonitkul | |
| 4,291,696 A | 9/1981 | Ring | |
| 4,294,253 A | 10/1981 | Friese | |
| 4,305,391 A | 12/1981 | Jackson | |
| 4,328,804 A | 5/1982 | Shimatani | |
| 4,361,151 A | 11/1982 | Fitzgerald | |
| 4,405,323 A | 9/1983 | Auerbach | |
| 4,479,791 A | 10/1984 | Sprague | |
| 4,676,773 A | 6/1987 | Sheldon | |
| 4,726,805 A | 2/1988 | Sanders, III | |
| 4,755,166 A | 7/1988 | Olmstead | |
| 4,787,895 A | 11/1988 | Stokes et al. | |
| 4,816,100 A | 3/1989 | Friese | |
| 4,891,042 A | 1/1990 | Melvin et al. | |
| 4,911,687 A | 3/1990 | Stewart et al. | |
| 4,960,417 A | 10/1990 | Tarr et al. | |
| 5,165,152 A | 11/1992 | Kramer et al. | |
| 5,330,421 A | 7/1994 | Tarr et al. | |
| 5,346,468 A | 9/1994 | Campion et al. | |
| 5,374,258 A | 12/1994 | Lloyd et al. | |
| 5,403,300 A | 4/1995 | Howarth | |
| 5,445,605 A | 8/1995 | Pluss | |
| 5,531,674 A | 7/1996 | Frayman | |
| 5,542,914 A | 8/1996 | Van Iten | |
| 5,592,725 A | 1/1997 | Brinker | |
| 5,895,408 A | 4/1999 | Pagan | |
| 5,909,884 A | 6/1999 | Schwankhart | |
| 5,911,712 A | 6/1999 | Leutwyler et al. | |
| 6,177,608 B1 | 1/2001 | Weinstrauch | |
| 6,206,867 B1 | 3/2001 | Osborn et al. | |
| 6,310,269 B1 * | 10/2001 | Friese et al. | 604/379 |
| 6,358,235 B1 | 3/2002 | Osborn et al. | |
| 6,433,246 B1 | 8/2002 | Nguyen et al. | |
| 6,478,786 B1 | 11/2002 | Glaug et al. | |
| D485,354 S | 1/2004 | Carlin et al. | |
| 6,719,743 B1 | 4/2004 | Wada | |
| 6,748,634 B2 | 6/2004 | Nguyen et al. | |
| 6,755,808 B2 | 6/2004 | Balogh et al. | |
| 6,889,409 B2 | 5/2005 | Friese et al. | |
| 6,939,340 B1 | 9/2005 | Berges | |
| 6,953,456 B2 | 10/2005 | Fuchs et al. | |
| 7,059,026 B2 | 6/2006 | Friese et al. | |
| 7,070,585 B2 | 7/2006 | Jensen | |
| 7,087,045 B2 | 8/2006 | Jensen | |
| 7,338,483 B2 | 3/2008 | Carlin et al. | |
| 7,967,803 B2 | 6/2011 | Van Ingelgem et al. | |
| 8,029,485 B2 * | 10/2011 | Jensen | 604/385.17 |
| 8,460,262 B2 * | 6/2013 | Fung et al. | 604/385.18 |
| 8,468,662 B2 * | 6/2013 | Rolli et al. | 28/118 |
| 2001/0014348 A1 | 8/2001 | Schoelling | |
| 2002/0151859 A1 | 10/2002 | Schoelling | |
| 2002/0157222 A1 | 10/2002 | Friese et al. | |
| 2003/0097108 A1 | 5/2003 | Hasse et al. | |
| 2003/0176844 A1 | 9/2003 | Randall et al. | |
| 2003/0208180 A1 | 11/2003 | Fuchs et al. | |
| 2004/0030316 A1 | 2/2004 | Gubernick et al. | |
| 2004/0199137 A1 | 10/2004 | Lamb | |
| 2005/0055001 A1 | 3/2005 | Cazzato et al. | |
| 2005/0113780 A1 | 5/2005 | Gatto et al. | |
| 2005/0113783 A1 | 5/2005 | Carlin et al. | |
| 2005/0113787 A1 * | 5/2005 | Carlin | 604/385.18 |
| 2005/0113788 A1 | 5/2005 | Carlin | |
| 2005/0113789 A1 | 5/2005 | Jensen | |
| 2005/0113807 A1 * | 5/2005 | Carlin | 604/904 |
| 2005/0143708 A1 | 6/2005 | Hagberg et al. | |
| 2005/0177090 A1 | 8/2005 | Jensen | |
| 2005/0193536 A1 | 9/2005 | Ingelgem et al. | |
| 2005/0256511 A1 | 11/2005 | Chase et al. | |
| 2005/0277904 A1 | 12/2005 | Chase et al. | |
| 2005/0283128 A1 | 12/2005 | Chase et al. | |
| 2006/0111662 A1 | 5/2006 | Karapasha et al. | |
| 2006/0167429 A1 | 7/2006 | Denti et al. | |
| 2006/0167430 A1 | 7/2006 | Denti et al. | |
| 2006/0241556 A1 | 10/2006 | Lochte et al. | |
| 2007/0083182 A1 | 4/2007 | Schoelling | |
| 2008/0154176 A1 | 6/2008 | Van Ingelgem et al. | |
| 2008/0154222 A1 * | 6/2008 | Chaffringeon | 604/361 |
| 2008/0195029 A1 | 8/2008 | Van Ingelgem et al. | |
| 2008/0200892 A1 | 8/2008 | Van Ingelgem et al. | |
| 2008/0221502 A1 | 9/2008 | Binner et al. | |
| 2009/0024103 A1 | 1/2009 | Van Ingelgem et al. | |
| 2009/0082712 A1 | 3/2009 | Hasse | |
| 2010/0121251 A1 | 5/2010 | Van Ingelgem et al. | |
| 2010/0318053 A1 | 12/2010 | Smet | |
| 2011/0201992 A1 | 8/2011 | Smet et al. | |
| 2011/0230854 A1 | 9/2011 | Smet | |
| 2011/0238028 A1 | 9/2011 | Smet | |
| 2012/0010587 A1 | 1/2012 | Smet | |
| 2012/0089111 A1 | 4/2012 | Magnusson et al. | |

FOREIGN PATENT DOCUMENTS

| | | |
|---|---|---|
| DE | 4 304 505 | 8/1994 |
| DE | 4 325 220 | 2/1995 |
| DE | 103 06 678 | 8/2004 |
| DE | 20320992 | 8/2005 |
| DE | 10 2005 030 182 | 1/2007 |
| DE | 10 2005 050514 | 4/2007 |
| EP | 0355 396 | 2/1990 |
| EP | 0422 660 | 4/1991 |
| EP | 0639 363 | 2/1995 |
| EP | 0 692 233 | 1/1996 |
| EP | 1 027 874 | 8/2000 |
| EP | 1 108 408 | 6/2001 |
| EP | 1 208 827 | 5/2002 |
| EP | 1459720 A | 9/2004 |
| EP | 1 481 656 | 12/2004 |
| EP | 1498093 | 1/2005 |
| EP | 1 547 554 | 6/2005 |
| EP | 1 547 555 | 6/2005 |
| EP | 1683503 | 7/2006 |
| EP | 1695 680 | 8/2006 |
| EP | 1704841 | 9/2006 |
| GB | 2120945 | 12/1983 |
| WO | WO 91/06272 | 5/1991 |
| WO | WO 96/27353 | 9/1996 |
| WO | WO 00/53141 | 9/2000 |
| WO | WO 02/49686 | 6/2002 |
| WO | WO 02/076357 | 10/2002 |
| WO | WO 02/078586 | 10/2002 |
| WO | WO 2005/063162 | 7/2005 |

(56) References Cited

FOREIGN PATENT DOCUMENTS

| WO | WO 2007/088057 | 8/2007 |
|----|----------------|--------|
| WO | WO 2009/129910 | 10/2009 |

OTHER PUBLICATIONS

International Search Report for International Application No. PCT/US2005/017884, mailed on Apr. 28, 2006.
International Search Report for International Application No. PCT/EP2006/000407, mailed on Apr. 20, 2006.
Search Report dated Apr. 28, 2006 from International Patent Application No. PCT/EP2006/001598.
International Search Report for International Application No. PCT/EP2006/002075, mailed on Jun. 7, 2006.
International Search Report for International Application No. PCT/EP2007/00872, mailed on Jul. 6, 2007.
International Search Report for International Application No. PCT/EP2008/051418, mailed on Jul. 31, 2008.
International Search Report for International application No. PCT/EP2009/063998, dated Mar. 11, 2010 by European Patent Office.
International Search Report for International application No. PCT/EP2009/065089, dated Jun. 9, 2010 by European Patent Office.
International Search Report for International application No. PCT/EP2009/067047, dated Feb. 17, 2010 by European Patent Office.
Search Report dated Jun. 4, 2004 from European Patent Application No. 03447303.
Partial Search Report dated Aug. 17, 2005 from European Patent Application No. 05447004.
Partial Search Report dated Nov. 14, 2005 from European Patent Application No. 05447042.
Search Report dated Nov. 10, 2005 from European Patent Application No. 05447065.
European Search Report dated Jan. 20, 2011 from European patent Application No. EP10169007.1.
Office Action dated Jan. 23, 2007 from U.S. Appl. No. 11/021,671, filed Dec. 22, 2004.
Office Action dated Jul. 11, 2007 from U.S. Appl. No. 11/021,671, filed Dec. 22, 2004.
Office Action dated Mar. 6, 2008 from U.S. Appl. No. 11/021,671, filed Dec. 22, 2004.
Office Action dated Nov. 28, 2008 from U.S. Appl. No. 11/021,671, filed Dec. 22, 2004.
Office Action dated Jun. 24, 2009 from U.S. Appl. No. 11/021,671, filed Dec. 22, 2004.
Office Action dated Mar. 18, 2010 from U.S. Appl. No. 11/021,671, filed Dec. 22, 2004.
Office Action dated Sep. 21, 2010 from U.S. Appl. No. 11/813,970, filed Feb. 8, 2008.
Final Office Action for U.S. Appl. No. 11/813,970 dated Mar. 17, 2011.
Office Action dated Sep. 30, 2009 from U.S. Appl. No. 11/816,908, filed Aug. 22, 2007.
Office Action dated May 13, 2010 from U.S. Appl. No. 11/816,908, filed Aug. 22, 2007.
Office Action dated Oct. 13, 2011 from U.S. Appl. No. 11/816,908, filed Aug. 22, 2007.
Office Action dated Sep. 21, 2009 from U.S. Appl. No. 11/909,250, filed Sep. 20, 2007.
Office Action dated Apr. 16, 2010 from U.S. Appl. No. 11/909,250, filed Sep. 20, 2007.
Office Action dated Sep. 22, 2010 from U.S. Appl. No. 12/278,228, filed Aug. 4, 2008.
Final Office Action for U.S. Appl. No. 12/278,228 dated Mar. 22, 2011.

\* cited by examiner

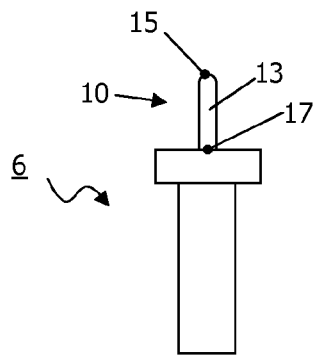
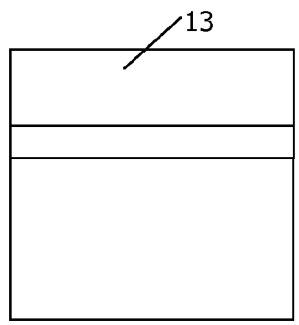
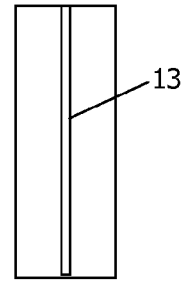
FIG. 18A     FIG. 18B     FIG. 18C
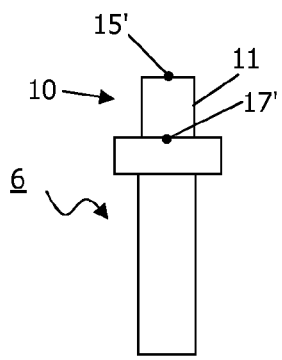
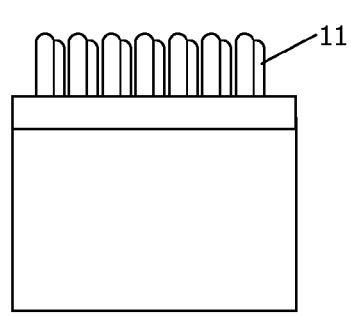
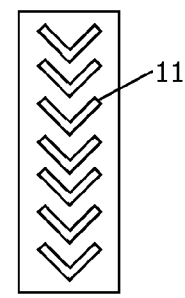
FIG. 19A     FIG. 19B     FIG. 19C
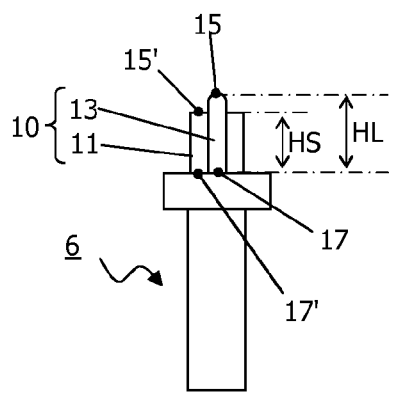
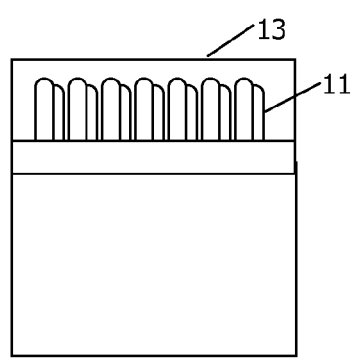
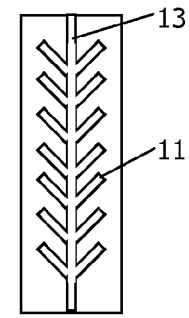
FIG. 20A     FIG. 20B     FIG. 20C

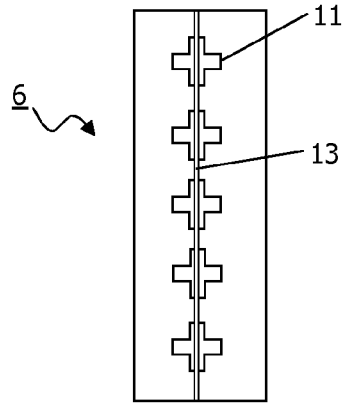
FIG. 23A
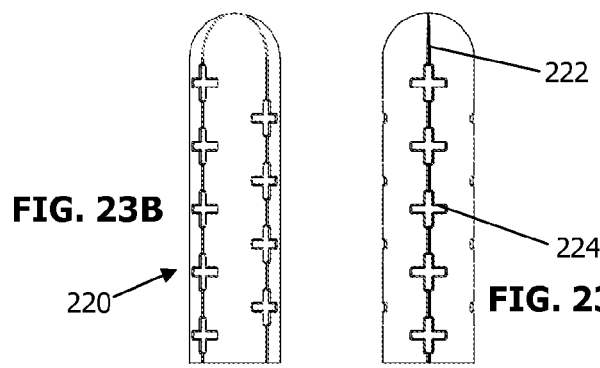
FIG. 23B
FIG. 23C
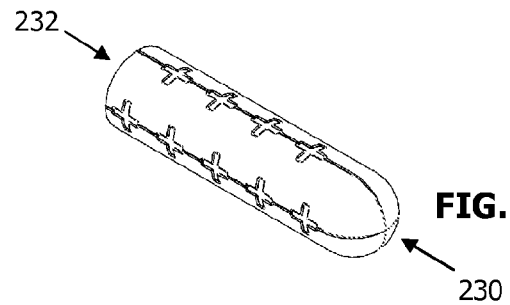
FIG. 23D
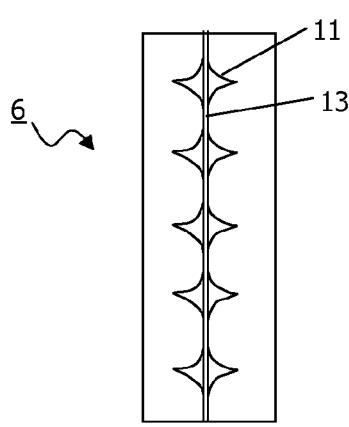
FIG. 24A
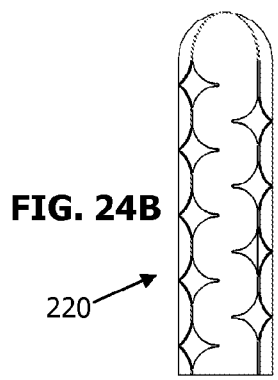
FIG. 24B
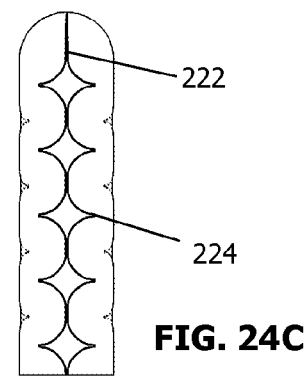
FIG. 24C
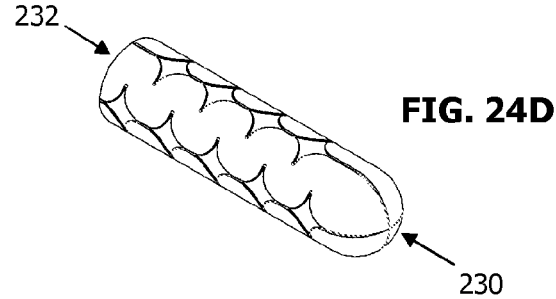
FIG. 24D

PRESS AND METHOD FOR PRODUCINIG ABSORBENT ARTICLE

CROSS-REFERENCE TO RELATED APPLICATIONS

This application is the U.S. National Phase under 35 U.S.C. §371 of International Application PCT/EP2011/061435, filed Jul. 6, 2011, which claims priority to EP 10169005.5, filed Jul. 9, 2010.

FIELD OF THE INVENTION

The invention concerns press and method for producing a tampon, in particular for feminine hygiene.

BACKGROUND TO THE INVENTION

From the prior art, cylindrical shaped tampons are foreseen having ribs defined by longitudinal grooves, and further provided with lateral grooves that cross the longitudinal grooves, as suggested, for example, in WO 2009/129910.

Presses and methods for manufacture having crossing grooves are said to rely on existing technology as described, for example, in EP 1 383 453 and DE 101 14 786. Such methods and presses tend to be slow or scuff the tampon surface, since they require a plurality of laterally-placed penetrating segments to form the cross grooves in a press jaw, that run counter to a smooth longitudinal ejection passage. WO 2009/129910 suggests no suitable method or press for production of the tampon.

There is a need for a new design of press and a method for manufacture of which overcomes the problems of the prior art.

AIMS OF THE INVENTION

The object of the invention is to provide a new type of tampon press and method for producing tampons with side grooves, including those with lateral crossing grooves known in the art. The tampons are produced more quickly and have little or no machine scuffing resulting in a smoother finish.

The advantages will become clear to the persons skilled in the art from the description and the accompanying figures provided below.

BRIEF DESCRIPTION OF THE FIGURES

FIG. 3, the jaws advance; FIG. 4 the jaws reach the closed position. FIG. 5 the jaws partially retract to a holding position; FIG. 6 the pressed blank tampon is slidably ejected; FIG. 7 the press jaws retract to the open position; FIG. 8 a new tampon blank is inserted into the press opening.

FIG. 11, the jaws advance; FIG. 12 the jaws reach the closed position. FIG. 13 the jaws partially retract to a holding position; FIG. 14 the pressed blank tampon is slidably ejected; FIG. 15 the press jaws retract to the open position; FIG. 16 a new tampon blank is inserted into the press opening.

FIGS. 18A to 18C depict a press jaw disposed with a penetrating segment for a longitudinal groove in side (FIG. 18A), front (FIG. 18B) and plan (FIG. 18C) views.

FIGS. 19A to 19C depict a press jaw disposed with penetrating segments for side grooves in side (FIG. 19A), front (FIG. 19B) and plan (FIG. 19C) views.

FIGS. 20A to 20C depict a press jaw disposed with combined penetrating segments for a longitudinal groove and a side groove in side (FIG. 20A), front (FIG. 20B) and plan (FIG. 20C) views.

FIGS. 21B to 21D depict numerous views of a finished tampon 220 pressed using a press comprising the press jaw depicted in FIG. 21A.

FIGS. 22B to 22D depict numerous views of a finished tampon 220 pressed using a press comprising the press jaw depicted in FIG. 22A.

FIG. 23A shows the plan view of the pressing end a press jaw 6, provided with a plurality of cross shaped penetrating segments for side grooves which cross a penetrating segment for a longitudinal groove.

FIGS. 23B to 23D depict numerous views of a finished tampon 220 pressed using a press comprising the press jaw depicted in FIG. 23A.

FIG. 24A shows the plan view of the pressing end a press jaw 6, provided with a plurality of diamond shaped penetrating segments for side grooves which cross a penetrating segment for a longitudinal groove, where the edges of the diamond are concave.

FIGS. 24B to 24D depict numerous views of a finished tampon 220 pressed using a press comprising the press jaw depicted in FIG. 24A.

SUMMARY OF SOME EMBODIMENTS OF THE INVENTION

Figure 1:
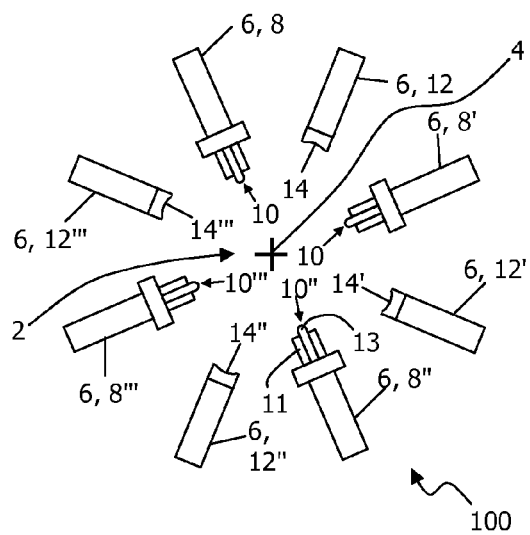
FIG. 1 shows in schematic form an arrangement of press jaws according to an embodiment of the invention, viewed along the press axis, where the jaws comprise alternately penetrating segments and pressing shoulders.

One embodiment of the invention is a press (100) for manufacturing a tampon, comprising at least three press jaws (6) arranged in a star around a central longitudinal press axis (4) forming a press opening (2), whereby there is provided on a single or separate adjacent press jaws (6):
- a penetrating segment, PSLG, (13) configured to penetrate the absorbing material with a longitudinal groove, and
- penetrating segments, PSSG, (11) configured to penetrate the absorbing material with a plurality of side grooves that are arranged in the longitudinal direction, wherein the press is configured to:
a) load a cylindrical blank (200) in the press opening (2),
b) move the press jaws (6) to a closed position to press the cylindrical blank (200) so forming a preform (210),
c) move the press jaws (6) to a holding position between the closed position and open position, so that the preform can be removed,
d) remove the preform while the jaws (6) are in the holding position, and
e) move the press jaws (6) to the open position for loading of a subsequent cylindrical blank.

Another embodiment of the invention is a press (100) as described above, wherein the press jaws are configured to move synchronously.

Another embodiment of the invention is a press (100) as described above, wherein each PSSG is in the shape essentially of a chevron (v-shaped), straight-edged slot, undulating, star, cross, diamond, circular, oval, triangle, rectangle, pentagon, sexagon, septagon, octagon, nonagon, decagon, other polygon, or the like.

Another embodiment of the invention is a press (100) as described above, wherein at least one PSSG is spatially separated from the PSLG when the press jaws are closed.

Another embodiment of the invention is a press (100) as described above, wherein at least one PSSG is in connection with the PSLG when the press are closed.

Another embodiment of the invention is a press (100) as described above, wherein the number of PSSGs disposed on a press jaw is between 3 and 7.

Another embodiment of the invention is a press (100) as described above, wherein the maximum height, HL, of the PLSG from the base (17) to the tip (15) is greater than the maximum height, HS, of the PSSG from the base (17) to the tip (15).

Another embodiment of the invention is a press (100) as described above, wherein the press jaws further comprise one or more pressing shoulders for finish shaping of the preform.

Another embodiment of the invention is a press (100) as described above, wherein during pressing, the pressing shoulders are configured to produce a preform having a mushroom-shape, domed head, constricted withdrawal end, conical withdrawal end, barrel shape, or a bullet shape.

Another embodiment of the invention is a press (100) as described above, wherein:
- each press jaw (6) is connected to a longitudinal transmission rod (50), aligned essentially radially to the press axis (4), or inclined to the radius centred on the press axis, said rod having a proximal end (56) closer to the press axis (4) and, at the opposing longitudinal side, a distal end (54) directed away from the press axis (4), and is configured for slidable linear displacement along an axis of movement (52) that is essentially radial to the press axis (4), or inclined to said radius.
- the press further comprises a rotatable annular plate (64) having a central axis in co-axial alignment with press axis (4) and provided with a plurality of discrete slots (66) on the plate (64), one slot for each rod, which slot engages with a roller (68) in revolute attachment to the distal end (54) of each rod (50), the roller (68) being in slidable connection with the slot (66), the axis of rotation of the roller (68) being perpendicular to the longitudinal axis of the rod (52) and is parallel with the press axis (4),
- the ring (60) is configured to rotate and thereby effect movement of the roller (68) and translation the rod (50) towards or away from the press axis (4) along the axis of movement (52), and
- the slot (66) shaped to retract or advance each press jaw (6) in the direction of the press axis (4) according to the angle of rotation of the annular plate (64) around its central axis.

Another embodiment of the invention is a press (100) as described above, wherein the press jaws (6) in step b) are moved to a closed position in a direction essentially radial or inclined to the radius of the press axis (4).

Another embodiment of the invention is a press (100) as described above, wherein the press jaws (6) in step c) are moved to a holding position between the closed position and open position, in which the tips (15') of the PSSGs (11) are retracted to a greater distance from the press axis (4) compared with the tips (15) of the PSLGs, such that the PSSGs are fully withdrawn from the preform, while contact is maintained between the preform longitudinal grooves and at least one PSLG (13).

Another embodiment of the invention is a press (100) as described above, wherein at least one side groove is spatially separated from adjacent side grooves.

Another embodiment of the invention is a process for manufacturing a tampon having a longitudinal axis, comprising the steps:
- inserting a cylindrical blank (200) of absorbing material in a press for manufacturing a tampon which presses absorbing material radially, which press comprises at least three press jaws (6) arranged in a star formation, whereby there is provided on a single or separate adjacent press jaws:
  - a penetrating segment, PSLG, configured to penetrate the absorbing material with a longitudinal groove, and
  - penetrating segments, PSSG, configured to penetrate the absorbing material with a plurality of side grooves that are arranged in the longitudinal direction, at least one side groove being spatially separated from adjacent side grooves,
- pressing the tampon blank in the press jaws, such that:
  - the PSLG penetrates the cylindrical blank to form longitudinal ribs (12) defined by longitudinal grooves, PSSG penetrate the cylindrical blank to form a plurality of side grooves that are spatially arranged and separated in the longitudinal direction, between, adjoining or crossing the longitudinal grooves, so forming a preform, moving the press jaws to a holding position between the closed position and open position, so that the preform can be removed, removing the preform from the press while the press jaws are maintained in the holding position.

Another embodiment of the invention is a process as described above, wherein the press is as defined above.

Another embodiment of the invention is a tampon obtainable by a process as described above.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The recitation of numerical ranges by endpoints includes all integer numbers and, where appropriate, fractions subsumed within that range (e.g. 1 to 5 can include 1, 2, 3, 4 when referring to, for example, a number of articles, and can also include 1.5, 2, 2.75 and 3.80, when referring to, for example, measurements). The recitation of end points also includes the end point values themselves (e.g. from 1.0 to 5.0 includes both 1.0 and 5.0).

In the following detailed description of the preferred embodiments, reference is made to the accompanying drawings that form a part hereof, and in which are shown by way of illustration only of specific embodiments in which the invention may be practiced. It is to be understood that other embodiments may be utilised and structural or logical changes may be made without departing from the scope of the present invention. The following detailed description, therefore, is not to be taken in a limiting sense, and the scope of the present invention is defined by the appended claims.

The present invention relates to a method and press for the manufacture of a tampon in particular for feminine hygiene having a longitudinal body in an essentially cylindrical shape. The tampon to be formed is divided into a number of longitudinal grooves that flank longitudinal ribs, and is provided with a plurality of side grooves on a rib arranged in the longitudinal direction. Preferably at least one side groove, preferable all are arranged between, adjoining or crossing the longitudinal grooves. When side grooves are disposed between two longitudinal grooves, at least one side groove, preferable all may be spatially separated from one or both flanking longitudinal grooves. The at least one side groove, preferably each and every side groove may also be spatially separated from other side grooves. When the side grooves are spatially separated, it means that the outer profile of each side groove on the surface of the tampon does not touch the outer profile of a neighbouring side groove on the surface of the tampon. Each side groove may project towards the core of the tampon, but may not enter the core.

The tampon is at least partially provided with longitudinal ribs defined by longitudinal grooves. The longitudinal ribs are preferably straight and preferably parallel to the longitudinal axis of the tampon, however, they may, alternatively, be straight and inclined to the longitudinal axis of the tampon. The number of longitudinal ribs can vary, for example depending on the diameter of the tampon and/or the type of absorption material. Preferably, there are between 4 and 12 ribs, more preferably there are between 6 and 12 ribs and even more preferably, at least eight. While the present invention, like many known tampons, may have an even number of ribs, it is also within the scope of the present invention to produce tampons with an odd number of ribs. The number of side grooves can vary, for example, depending on the length of the tampon and/or the type of absorption material. The number of side grooves may be equal to or at least 2, 3, 4, 5, 6, 7, 8, 9, 10, or 12 for a longitudinal groove or rib. Preferably, there are between 3 and 10 side grooves for a longitudinal groove or rib, more preferably between 4 and 7, most preferably 4 or 5. At least one rib, preferably each and every rib is provided with side grooves.

The side grooves 224 (e.g. FIG. 21B, C, D) in the tampon are essentially discrete indentations in the tampon surface that project towards the tampon core, and are disposed at the lateral sides of the longitudinal grooves. The terms indentations side groove and are considered synonymous. The indentations may have any shape, for example, a regular or irregular polygonal shape on the surface, or may take the form of lateral grooves. The side grooves 224 are suitable for channelling liquid into the tampon 220. Absorbency of the tampon 220 is, therefore, improved, because the surface is more open. After the introduction of the tampon into the body cavity, these side grooves 224 convey the body fluid directly to the fiber core, in order to utilize its fibrous material immediately to increase the absorption capacity and expansion capacity of the tampon and to accelerate the opening of the closed longitudinal grooves 222 outward. Therefore, the arrangement of the side grooves 224 and longitudinal grooves 222 brings about an enlargement of the surface of the tampon 220 which results in the absorption capacity and expansion capacity of the fiber core being improved considerably. Further, there is a more rapid take-up of body fluid. At the same time, a reduction in the weight of fibrous material used in the tampon is thus possible, which allows more economical production of the tampon.

The present invention concerns an apparatus, specifically a press, for manufacturing the tampon described above. In the prior art, pressing machines have penetrating segments, which form longitudinal ribs defined by longitudinal grooves and which penetrate the absorbing material. Such machines are known for example from EP 0 422 660, EP 0 639 363 and WO 02/078586 which are incorporated herein by reference.

The apparatus of the current invention comprises a press having press jaws each having a pressing end and opposite thereto a back end, which jaws are arranged in a star formation with respect to the press axis and preferably, but not necessarily, at the same radial distance from the press axis at least in the open position. The pressing end of the jaws are directed towards the press axis. The jaws can be moved (i.e. advanced and/or retracted) in a common plane, towards the press axis between an open position, holding position and closed position and, in their closed position, are preferably supported on one another on their mutually opposite longitudinal sides. The movement towards the press axis may be radial or inclined with the radius of the press axis.

The jaws preferably move synchronously to provide an enhanced geometric uniformity of the longitudinal grooves, side grooves and ribs. Accordingly, the integrity of the non-woven material surrounding the tampon blank is maintained. Tension is typically formed across a rib in the non-woven cover because the cover is stretched by its folding into the longitudinal grooves. The pressing of side grooves into the ribs would normally cause the cover to tear. However, by simultaneously pressing the longitudinal grooves and side grooves, tensions in the cover are evenly distributed. Preferably, the tampon blank is compressed such that said longitudinal ribs extend outward at equal circumferential angle intervals.

A preferred press consists of at least 3 press jaws, preferably 8 (4 PSLG+4 PSSG) press jaws. It is desirable to equip the press with an even number of press jaws (e.g. 2, 4, 6, 8), but other numbers of press jaws can be used, including odd numbers (e.g. or 3, 5, 7, 9). The number of press jaws can vary, for example depending on the weight and the composition of the material intended for the tampon and can also be smaller or greater than eight, although the number generally should not be under three. One or more penetrating segments for pressing the grooves are provided at the pressing end of the jaw. Arranged on the jaws at the pressing end are penetrating segment for pressing the longitudinal groove (PSLG) and penetrating segments for pressing the side grooves (PSSG) or indentations (PSI) where the terms PSSG and PSI are synonymous.

The press jaws may be arranged circumferentially in adjacent pairs, one jaw of the pair comprising at the pressing end a penetrating segment for pressing the longitudinal groove (PSLG) and the second jaw of the pair comprising at the pressing end penetrating segments for pressing the side grooves (PSSG). As such, the circumferential arrangement of jaws alternates (see FIGS. 9 to 16). The number of jaws in the press disposed with the PSLG is equal to the number disposed with the PSSG, which may be equal to or at least 2, 3, 4 pairs of press jaws.

Alternatively, the PSLG and PSSG may be disposed on the same, single press jaw, the PSSG arranged on either or both longitudinal sides of the PSLG (see FIGS. 1 to 8). This can give rise to a tampon where the longitudinal grooves and side grooves adjoin or cross. When the PSLG and PSSG are provided on the same press jaw, the number of jaws in the press may be equal to or at least 3, 4, 5, 6, 7, or 8. It is within the scope of the invention that the PSSGs are disposed on a plurality (e.g. at least 1, 2, 3, 4, 5, 6, 7, 8) of adjacent press jaws, which combine to form a larger PSSG that spans a larger circumferential arc that would be possible with a single press jaw.

It will be appreciated that pressing shoulders may be provided as separate press jaws, for example, alternating with jaws having penetrating segments (see FIGS. 1 to 8). According to one aspect of the invention, the press jaws may be arranged circumferentially in adjacent pairs, one jaw of the pair comprising at the pressing end the PSLG and PSSG and the second jaw of the pair comprising at the pressing end a pressing shoulder. When the PSLG and PSSG are provided on the same press jaw, the number of jaws in the press including jaws containing the pressing shoulder may be equal to or at least 3, 4, 5, 6, 7, or 8. In an alternative arrangement, the pressing shoulder may be combined with press jaws disposed with penetrating segments. For instance, a press jaw may have a pressing shoulder provided with penetrating segments for pressing the side grooves (PSSG). In the alternative, a press jaw may have a combination of one PSLG and a pressing shoulder arranged on either or both sides of the PSLG, the pressing shoulder optionally provided with the PSSG. It is well understood in the art that the pressing shoulder is a shaping tool for finish shaping of the preform, that applies radial pressure on the circumferential surface of the ribs of the perform subsequent to impression of the tampon by the penetrating segments. The pressing shoulders can be straight or angular, but preferably have a curvature in the transversal direction in order to press the circumferential surface of the tampon blank into an essentially cylindrical form of smaller diameter. A pressing shoulder may contain one or more slots to accommodate the PSSGs of a neighbouring jaw in a closed position (i.e. fitting complementary arrangement).

It is an aspect of the invention that the press jaws can be moved into an open, closed and a holding position that is between the closed and open position. In the open position, the opening formed in the press is of sufficient size for insertion of a tampon blank. In the closed position, the tampon blank is pressed. In the holding position, the preform is suspended on the tips of at least one (preferably at least two) penetrating segments (PSLGs), and can be removed (ejected) axially from the press, preferably slidably, without significant damage. By arranging a slidable ejection while the tampon is suspended by the tips of the penetrating segments (PSLGs), the integrity of the tampon is maintained, avoiding damage to its surface by otherwise protruding PSSGs in the ejection passage. Equally, ejection of the tampon while the jaws are open fully would lead to damage as the space between two jaws into which the tampon is released provides only an obstructive and unhygienic passage for slidable ejection.

According to one aspect of the invention, the PSLG and PSSG retract differentially subsequent to pressing the preform. The PSSG retracts to a greater extent than the PSLG after pressing and prior to ejection of the preform so formed. In other words, the press jaws are retracted to the holding position between the closed position and the open position of the jaws, in which the tips of the PSSGs are moved (retracted) to a greater distance from the press axis compared with the tips of the PSLGs, such that the PSSGs are withdrawn from the preform, while contact is substantially maintained between the preform longitudinal grooves and at least one (preferably at least two) PSLGs. The PSSGs may be fully withdrawn from the preform.

The differential retraction allows removal (ejection) of the tampon longitudinally while the jaw is still partially closed. At the moment of ejection, the press jaws open partially to a holding position in which the PSSGs are fully withdrawn and clear of the preform, while the PSLGs maintain contact with the tampon longitudinal grooves. Thus, the tampon is suspended in the partially closed jaws by the circumferential arrangement of PSLGs, but is free from contact with the PSSGs. Accordingly, the tampon can be propelled and ejected longitudinally while in slidable contact only with the star-shaped arrangement of PSLGs. By arranging a slidable ejection along the PSLGs, the integrity of the tampon is maintained, avoiding damage to its surface by otherwise protruding PSSGs in the ejection passage.

Differential retraction of the penetrating segments may be achieved by differential lengths of the respective PSLG and PSSG i.e. the PSLG is longer than the PSSG. This is illustrated in FIGS. 18A to 20A, where the maximum height, HL, of the PSLG from the base 17 to the tip 15 is greater than the maximum height, HS, of the PSSG from the base 17' to the tip 15'. Accordingly, the jaws may be configured to retract synchronously by an equal distance until the holding position is maintained. Alternatively, differential retraction may be achieved by different radial press jaw lengths or by retracting the respective press jaws by different amounts; this applies when the PSLG and PSSG are disposed on separate press jaws.

One embodiment of the invention is a press 100 for manufacturing a tampon, comprising at least three press jaws 6 arranged in a star around a central longitudinal press axis 4 forming a press opening 2, whereby there is provided on a single or separate adjacent press jaws 6:

a penetrating segment, PSLG, 13 configured to penetrate the absorbing material with a longitudinal groove, and penetrating segments, PSSG, 11 configured to penetrate the absorbing material with a plurality of side grooves that are arranged in the longitudinal direction, wherein the press is configured, preferably sequentially, to:
a) load a cylindrical blank 200 in the press opening 2,
b) move the press jaws 6 to a closed position to press the cylindrical blank 200 so forming a preform 210,
c) move the press jaws 6 to a holding position between the closed position and open position, so that the preform can be removed,
d) remove the preform while the jaws (6) are in the holding position, and
e) move the press jaws 6 to the open position for loading of a subsequent cylindrical blank.

Besides being arranged in the longitudinal direction, at least one, preferably each and every side groove may also be spatially separated from other or adjacent side grooves. As mentioned elsewhere, at least one, preferably each and every side groove may adjoin or cross adjacent longitudinal grooves. At least one, preferably each and every side groove may be in spatially separated from one or both adjacent longitudinal grooves. In step b) the press jaws 6 is moved (advanced) to a closed position to press the cylindrical blank 200, so forming a preform 210. The movement, towards the press axis, is preferably radial or may be inclined to the radius of the press axis. The cylindrical blank is, thus, pressed radially or may be pressed inclined to the radius of the press axis.

In step c), the press jaws 6 are moved (retracted) to a holding position between the closed position and open position, so that the preform can be axially removed, preferably without substantial obstruction. Preferably, the holding position is where the tips 15' of the PSSGs 11 are moved (retracted) to a greater distance from the press axis 4 compared with the tips 15 of the PSLGs, such that the PSSGs are withdrawn, preferably fully, from the preform, while contact is maintained between the preform longitudinal grooves and at least one (Preferably at least two) PSLGs 13.

In step d) the preform is axially removed (ejected), preferably slidably, while the jaws (6) are in the holding position, In step e) the press jaws 6 are moved (retracted) to the open position for loading of the next cylindrical blank. The sequence a) to e) may be repeated for a subsequent cylindrical blank.

The penetrating segment for pressing the longitudinal groove (PSLG) is configured to press essentially longitudinal grooves into the blank tampon. It is provided at the pressing end of the press jaw. The longitudinal grooves extend at least partially, preferably fully, from the insertion end to the withdrawal end, and are preferably parallel to the press axis. The PSLG, is a straight, blunt blade having a tip oriented towards the press opening. It is longitudinal and preferably the longitudinal length is aligned with the press axis, but may equally be inclined to the press axis. Preferably, when the press jaw is closed, each PSLG is orientated in the cutting direction radially or inclined to the radius of the press axis, thereby giving rise to radial or radially-inclined grooves in the tampon. The height, HS, of the PSLG from its base to the tip (FIG. 20A) may be 10%, 20%, 30% 40%, 50%, 60%, 70%, 80%, or 90% greater than the height of the PSSG, or greater by value in the range between any two of the aforementioned values. Preferably, the height of the PSLG is essentially constant along the longitudinal length of the press jaw.

With reference to FIGS. 18A to C which depict a press jaw 6 in side (18A), front (18B) and plan (18C) views, the PSLG 13 is provided on the pressing end of the press jaw 6 and is an essentially planar oblong structure protruding from the base of the pressing end. According to one aspect of the invention, the transverse profile of the PSLG may be symmetrical along its length (from base 17 to tip 15) as is shown, for example, in FIG. 18A, reference sign 13. Alternatively, the penetrating segment may be asymmetric along its length, wherein one edge of the penetrating segment is straight and the other curved.

The penetrating segments for pressing the side groove (PSSG) are disposed on at least one lateral side of a PSLG when the press jaws are closed. The PSSGs are configured to press a plurality of side grooves into the blank, which side grooves are arranged in the longitudinal direction of the press jaw. At least one, preferably each and every PSSG is spatially separated (i.e. isolated) from other PSSGs in the longitudinal direction. The side grooves may be provided exclusively on a rib flanked by two longitudinal grooves, or may adjoin a longitudinal groove, or both. The side grooves may or may not cross a longitudinal groove. Each and every side groove may have the same profile (e.g. chevron, star, cross), or at least two side grooves may have different profiles (e.g. chevron, star) Preferably side grooves are arranged between at least one pair, preferably each and every pair of longitudinal grooves, or are arranged adjoining or crossing at least one, preferably each and every longitudinal groove. In the present description, considerations of the side grooves such as profile, spatial separation and circumferential width (CW) are made without regard to the longitudinal groove when the side groove adjoins or crosses a longitudinal groove.

The PSSG comprise a plurality of blunt blades each having a tip 15' oriented towards the press opening, and arranged in the direction of the press axis. Preferably, at least one PSSG, preferably each and every PSSG is spatially separated (i.e. isolated) from another PSSGs in the longitudinal direction. By spatially separated, it is meant that at least the tip 15', preferably the body of each PSSG does not contact the tip 15', preferably the body, of any neighbouring PSSG in the longitudinal direction on the press jaw. Preferably, when the press jaw is closed, the cutting direction of each PSSG is orientated radially or inclined to the radius of the press axis, thereby giving rise to radial or radially-inclined grooves in the tampon. The height, HS, of the PSSG from its base to the tip (FIG. 20A) may be a percentage of the height of the PSLG, which percentage is 10%, 20%, 30%, 40%, 50%, 60%, 70%, 80%, or 90% or a value in the range between any two of the aforementioned values. With reference to FIGS. 19A to C which depicts a press jaw 6 in side (19A), front (19B) and plan (19C) views, the PSSGs 11 are provided on the pressing end of the press jaw 6 and are comprised in a plurality protruding chevrons (FIG. 19C) spatially separated in the longitudinal direction of the jaw. Preferably each PSSG has the same shape (e.g. chevron, star, cross). Preferably the PSSGs are arranged between, adjoining or crossing each and every PSLG.

Figure 29:
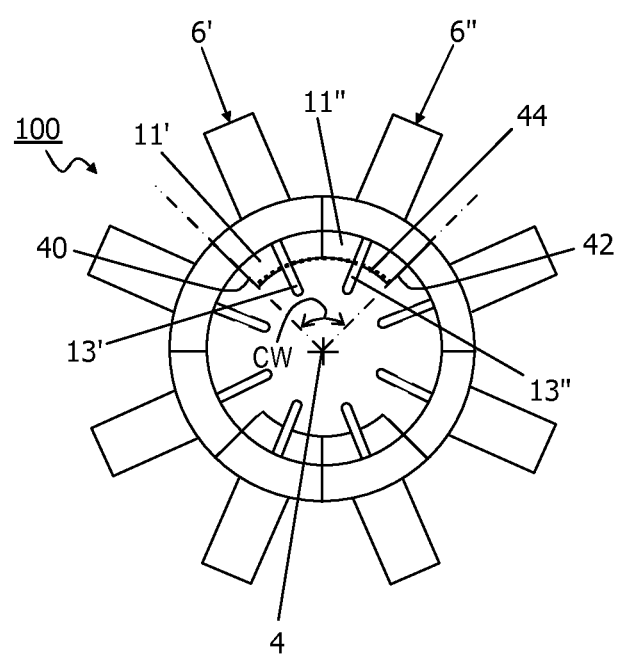
FIG. 29 Schematic form an arrangement of press jaws in the closed position according to an embodiment of the invention, viewed along the press axis, where two adjoining press jaws each comprise a penetrating segment for a side groove that together form a larger continuous penetrating segment for a side groove.

The circumferential width in degrees, CW, of a PSSG is the angle adopted by the arc centred on the press axis, and bound by the lateral ends of the combined PSSGs when the press jaws are closed, and which is measured in a plane tangential to the press axis. It will be appreciated, that the penetrating segment for a side groove may be formed by one or the combination of several adjacent press jaws (e.g. 1, 2, 3, 4, 5, 6, 7, 8). As such, the CW may adopt any angle and can circumnavigate the entire (360 deg) tampon if required. According to one aspect of the invention, the CW of a PSSG is 2, 4, 5, 6, 8, 10, 12, 14, 16, 18, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360 degrees, or a value in the range between any two of the aforementioned values. FIG. 29 depicts the CW dimension of a PSSG in a press 100 having jaws 6, 6', 6" in a closed position, wherein two PSSGs 11', 11" of adjacent press jaws 6', 6" combine to form a single, elongated PSSG. The arc, 44, centred on the press axis 4, is defined by the lateral ends 40, 42 of the combined PSSG 11', 11", which arc gives rise to the CW measurement that is angle of the arc.

FIGS. 20A to 20C depict a press jaw 6 in side (20A), front (20B) and plan (20C) views, the PSLG 13 is provided on the pressing end of the press jaw 6 flanked by chevron-shaped PSSGs 11 in crossing alignment with the PSLG 13, which PSSGs 11 are spatially separated in the longitudinal direction of the jaw. The overall pattern is a herringbone (FIG. 20C). According to one aspect of the invention, the transverse profile of the PSSG may be symmetrical along its length (from base to tip). Alternatively PSSG may be asymmetric along its length, wherein one edge of the penetrating segment is straight and the other curved.

The PSSG may have any suitable profile, for example, essentially of a chevron (v-shaped), straight-edged slot, undulating, star, cross, diamond, circular, oval, triangle, rectangle, pentagon, sexagon, septagon, octagon, nonagon, decagon, other polygon, or the like. At least on, preferably each and every PSSG may be spatially separated from one or both flanking PSLGs; where there is spatial separation from both flanking PSLGs, the side groove will be present in the longitudinal ribbed part of the tampon only. Alternatively, at least one, preferably each and PSSG may be in connection with a flanking PSLG, in which case the side groove will touch or cross the adjoining longitudinal groove of the tampon. Examples of different configurations of the PSSG are given in FIGS. 21A to 28D.

Figure 21A:
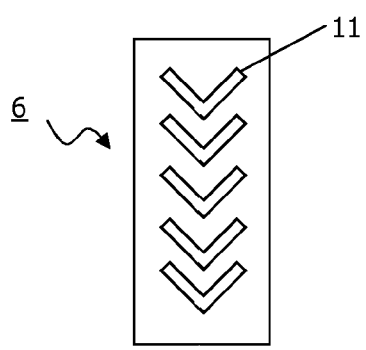
FIG. 21A shows the plan view of the pressing end a press jaw 6, provided with a plurality of chevron shaped penetrating segments for side grooves.
Figure 21D:
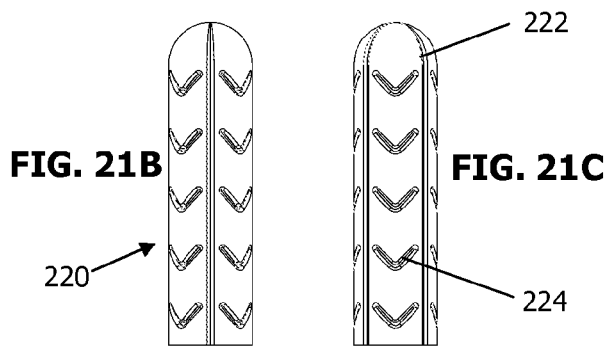
Figure 21D:
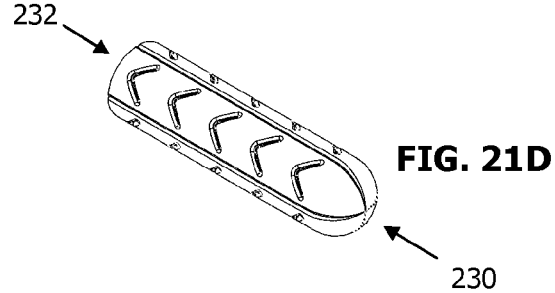

FIG. 21A shows the plan view of the pressing end a press jaw 6, provided with a plurality of chevron shaped PSSGs 11 spatially separated in the longitudinal direction of the jaw 6. FIGS. 21B to 21D depict numerous view of a finished tampon 220 having a rounded insertion end 230 and a withdrawal end 232, pressed using a press comprising the press jaw depicted in FIG. 21A. It has four longitudinal grooves 222, formed by the PSLGs (not shown), and a plurality of chevron shaped side grooves 224 spatially separated in the longitudinal direction of the tampon 220.

Figure 22A:
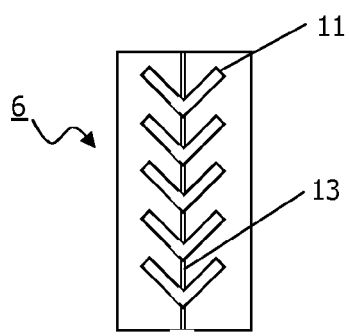
FIG. 22A shows the plan view of the pressing end a press jaw 6, provided with a plurality of chevron shaped penetrating segments for side grooves which cross a penetrating segment for a longitudinal groove, whereby the apex of each chevron point towards the insert end.
Figure 22D:
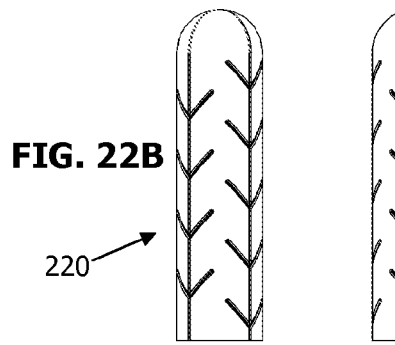
Figure 22D:
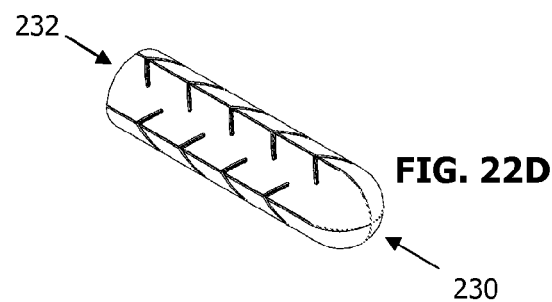

FIG. 22A shows the plan view of the pressing end a press jaw 6, provided with a plurality of chevron shaped PSSGs 11 spatially separated in the longitudinal direction of the jaw 6, which cross a PSLG 13 along the chevron apex. FIGS. 22B to 22D depict numerous views of a finished tampon 220 having a rounded insertion end 230 and a withdrawal end 232, pressed using a press comprising the press jaw depicted in FIG. 22A. It has four longitudinal grooves 222, formed by the PSLGs 13, and a plurality of chevron shaped side grooves 224 spatially separated in the longitudinal direction of the tampon 220 each of which cross the longitudinal grooves at its apex. The result is a herring bone pattern on the tampon 220.

FIG. 23A shows the plan view of the pressing end a press jaw 6, provided with a plurality of cross-shaped PSSGs 11 spatially separated in the longitudinal direction of the jaw 6, which cross the PSLG 13 along the centre of the cross and through two opposing corners of the cross. FIGS. 23B to 23D depict numerous views of a finished tampon 220 having a rounded insertion end 230 and a withdrawal end 232, pressed using a press comprising the press jaw depicted in FIG. 23A. It has four longitudinal grooves 222, formed by the PSLGs 13, and a plurality of cross-shaped side grooves 224 spatially separated in the longitudinal direction of the tampon 220 each of which cross the longitudinal grooves at the centre of the cross and through two opposing branches of the cross.

FIG. 24A shows the plan view of the pressing end a press jaw 6, provided with a plurality of diamond-shaped PSSGs 11 spatially separated in the longitudinal direction of the jaw 6, which cross the PSLG 13 along the centre of the cross; the diamond has concave edges. FIGS. 24B to 24D depict numerous views of a finished tampon 220 having a rounded insertion end 230 and a withdrawal end 232, pressed using a press comprising the press jaw depicted in FIG. 24A. It has four longitudinal grooves 222, formed by the PSLGs 13, and a plurality of diamond-shaped side grooves 224 spatially separated in the longitudinal direction of the tampon 220 each of which cross the longitudinal grooves through the centre of the diamond and through two opposing corners of the diamond.

Figure 25A:
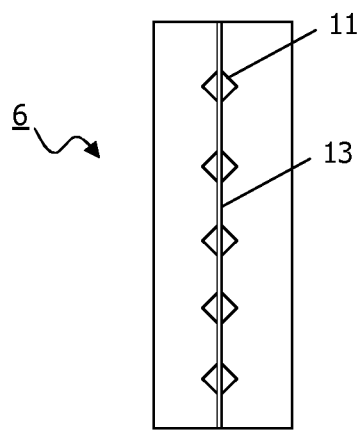
FIG. 25A shows the plan view of the pressing end a press jaw 6, provided with a plurality of diamond shaped penetrating segments for side grooves which cross a penetrating segment for a longitudinal groove.
Figure 25B:
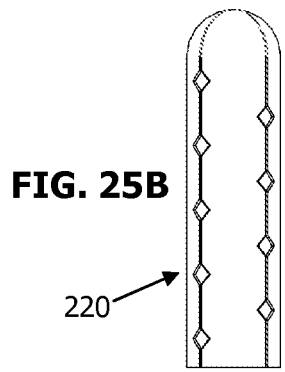
FIGS. 25B to 25D depict numerous views of a finished tampon 220 pressed using a press comprising the press jaw depicted in FIG. 25A.
Figure 25C:
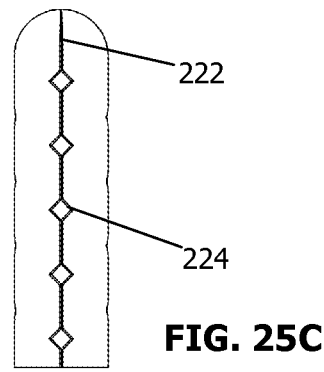
Figure 25D:
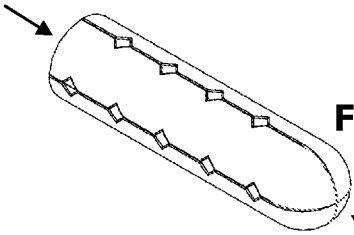

FIG. 25A shows the plan view of the pressing end a press jaw 6, provided with a plurality of diamond-shaped PSSGs 11 spatially separated in the longitudinal direction of the jaw 6, which cross the PSLG 13 along the centre of the diamond and through two opposing corners of the diamond; the diamond has straight edges. FIGS. 25B to 25D depict numerous views of a finished tampon 220 having a rounded insertion end 230 and a withdrawal end 232, pressed using a press comprising the press jaw depicted in FIG. 25A. It has four longitudinal grooves 222, formed by the PSLG 13, and a plurality of diamond side grooves 224 spatially separated in the longitudinal direction of the tampon 220 each of which cross the longitudinal grooves at the centre of the diamond and through two opposing corners of the diamond.

Figure 26A:
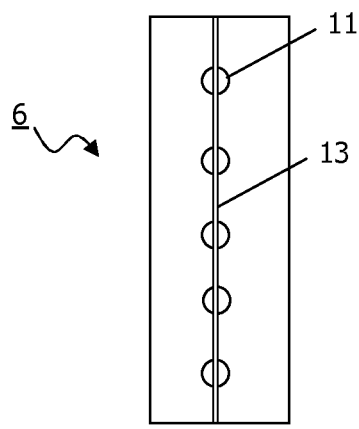
FIG. 26A shows the plan view of the pressing end a press jaw 6, provided with a plurality of circular penetrating segments for side grooves which cross a penetrating segment for a longitudinal groove.
Figure 26B:
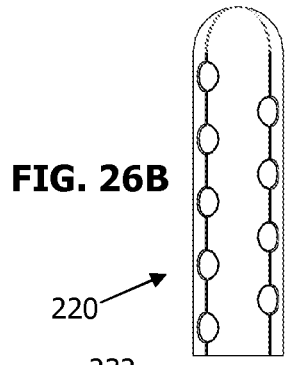
FIGS. 26B to 26D depict numerous views of a finished tampon 220 pressed using a press comprising the press jaw depicted in FIG. 26A.
Figure 26C:
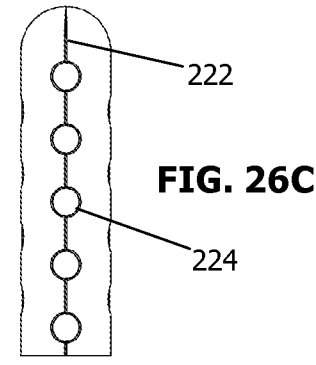
Figure 26D:
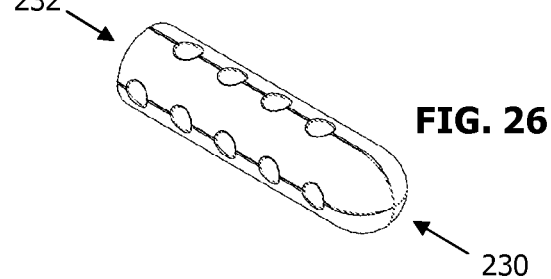

FIG. 26A shows the plan view of the pressing end a press jaw 6, provided with a plurality of circular PSSGs 11 spatially separated in the longitudinal direction of the jaw 6, which cross the PSLG 13 along the centre of the circle. FIGS. 26B to 26D depict numerous views of a finished tampon 220 having a rounded insertion end 230 and a withdrawal end 232, pressed using a press comprising the press jaw depicted in FIG. 26A. It has four longitudinal grooves 222, formed by the PSLG 13, and a plurality of circular side grooves 224 spatially separated in the longitudinal direction of the tampon 220 each of which cross the longitudinal grooves at the centre of the circle.

Figure 27A:
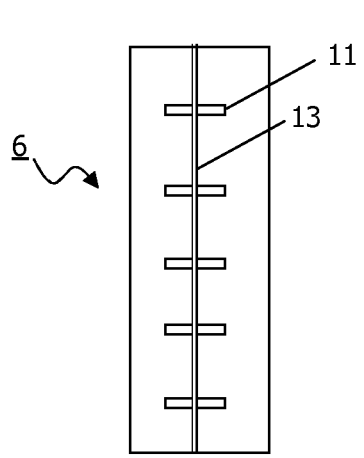
FIG. 27A shows the plan view of the pressing end a press jaw 6, provided with a plurality of straight-edged slot shaped penetrating segments for side grooves which cross a penetrating segment for a longitudinal groove.
Figure 27B:
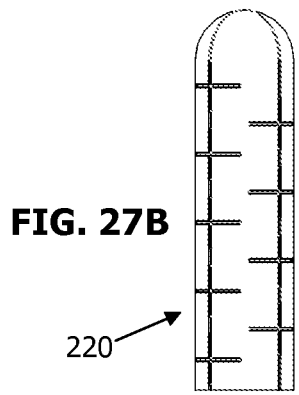
FIGS. 27B to 27D depict numerous views of a finished tampon 220 pressed using a press comprising the press jaw depicted in FIG. 27A.
Figure 27C:
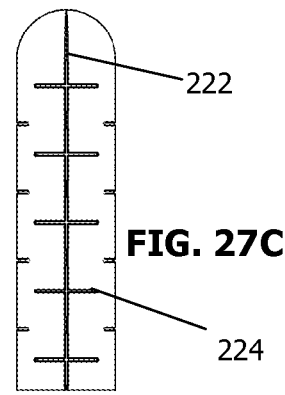
Figure 27D:
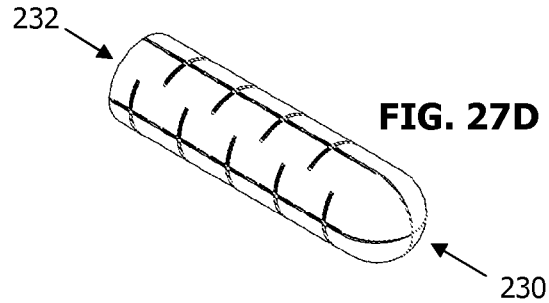
Figure 28A:
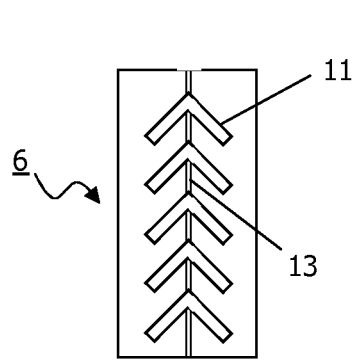
FIG. 28A shows the plan view of the pressing end a press jaw 6, provided with a plurality of chevron shaped penetrating segments for side grooves which cross a penetrating segment for a longitudinal groove, whereby the apex of each chevron point towards the insert end.
Figure 28B:
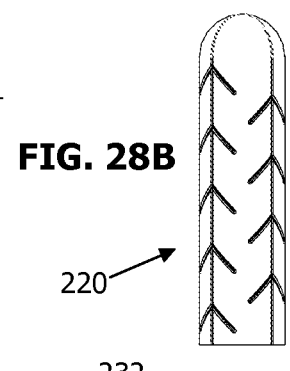
FIGS. 28B to 28D depict numerous views of a finished tampon 220 pressed using a press comprising the press jaw depicted in FIG. 28A.
Figure 28C:
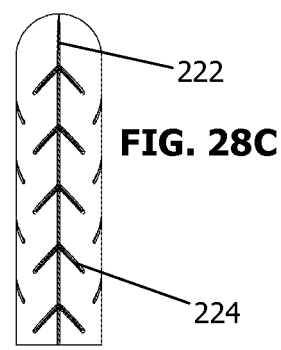
Figure 28D:
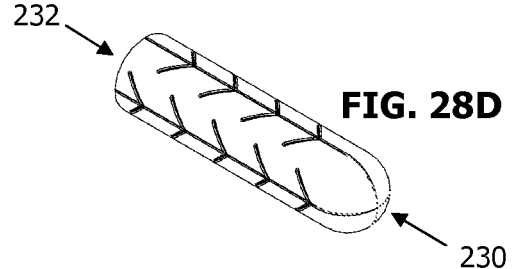

FIG. 27A shows the plan view of the pressing end a press jaw 6, provided with a plurality of straight-edged slot shaped PSSGs 11 spatially separated in the longitudinal direction of the jaw 6, which cross the PSLG 13 along the centre of the long length of the slot. FIGS. 27B to 27D depict numerous views of a finished tampon 220 having a rounded insertion end 230 and a withdrawal end 232, pressed using a press comprising the press jaw depicted in FIG. 27A. It has four longitudinal grooves 222, formed by the PSLG 13, and a plurality of slot-shaped side grooves 224 spatially separated in the longitudinal direction of the tampon 220 each of which cross the longitudinal grooves at the centre of the long length of the slot.

FIGS. 28A to 28D are similar to FIGS. 22A to 22D except the direction of the chevron is reversed, i.e. the apex of each chevron is directed towards the insertion end 230 of the tampon in FIGS. 28A to 28D, compared with FIGS. 22A to 22D where the apex of each chevron is directed towards the withdrawal end 232.

An embodiment of a press apparatus 100 of the current invention and the method is described in more detail below and exemplified by FIGS. 1 to 8. FIG. 1 shows the press jaws of an embodiment of press 100 according to the invention in open position. There are two groups of jaws 6, the first group 8, 8', 8", 8'" provided with penetrating segments 10, 10', 10", 10'", the second group 12, 12', 12", 12'", provided with pressing shoulders 14, 14', 14", 14'" facing the press opening 2. The first 8, 8', 8", 8'" and second group 12, 12', 12", 12'" of jaws alternate circumferentially. The penetrating segments of the first group 8, 8', 8", 8'" each comprise a PSLG 13, crossed by a plurality of PSSGs 11.

While the embodiment in FIGS. 1 to 8 show penetrating segments restricted to every other press jaw, it is also within the scope of the invention that each and every jaw is provided with a penetrating segment as explained elsewhere and as shown in FIGS. 9 to 16. The press jaws 6 are arranged in a star formation around the press axis 4. The PSLG in profile are shown to have a greater maximum height (HL) compared with the maximum height (HS) of the PSSGs.

Figure 2:
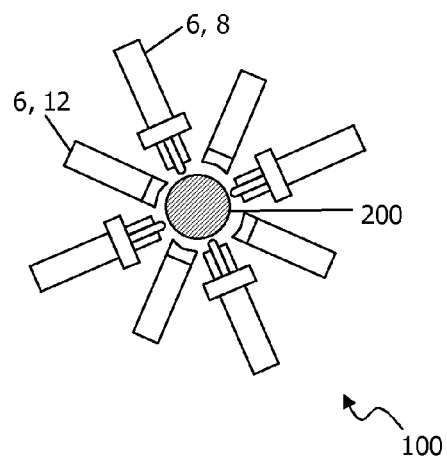
FIGS. 2 to 8 depict a pressing cycle, FIG. 2, tampon blank is inserted into a press opening.
Figure 3:
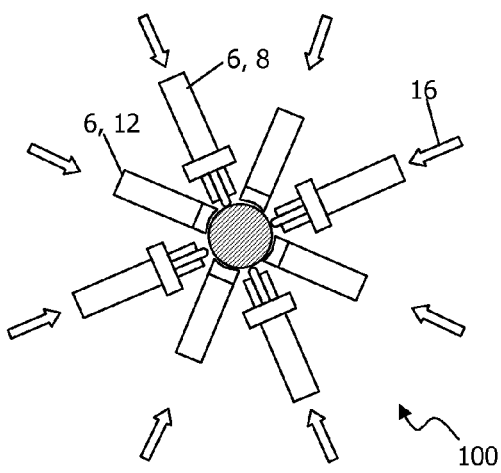
Figure 4:
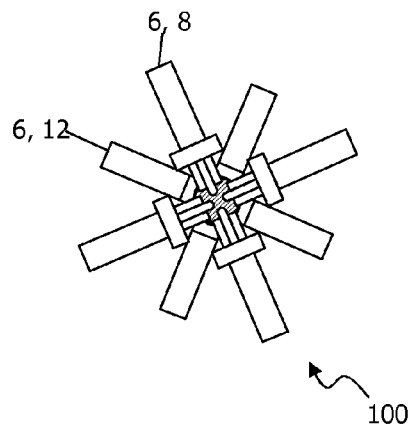
Figure 5:
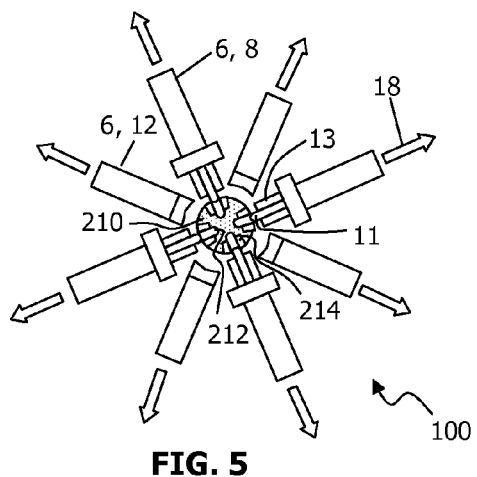
Figure 8:
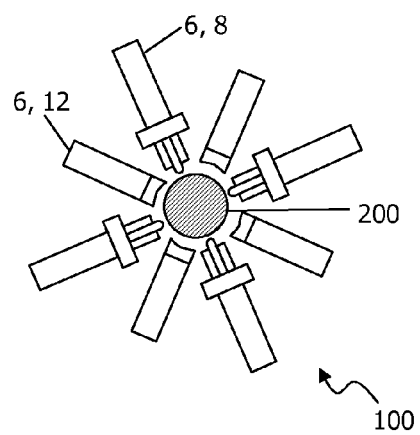

The pressing cycle depicted in FIGS. 2 to 8 is described in more detail as follows. FIG. 2 shows the press 100 with a blank tampon 200 inserted in the press opening 2. The press jaws 6 synchronously advance 16 radially towards the press axis 4 (FIG. 3), penetrating and pressing the tampon blank 200 as depicted in FIG. 4. While the FIG. 4 does not show the jaws supported on one another on their mutually opposite longitudinal sides in the closed position, this aspect is preferable and within the scope of the invention. In FIG. 5 the press jaws are retracted 18 to a holding position, to the extent that the PSSG 11 are entirely withdrawn from the preform 210 so produced, in particular from the side grooves 214, while the PSLG 13 remain in contact with the longitudinal grooves 212. In that holding position, the preform 210 is ejected (FIG. 6) by means of a ram (not shown) that slidably propels the preform along the tips of the PSLG 13, parallel to the press axis 4 and out towards the other side of the press 100. The press jaws fully retract 20 (FIG. 7), sufficient to allow insertion of a new tampon blank 200 (FIG. 8). The grooves 212, 214 in the preform 210 have been enlarged for clarity in the drawings; in practice, the grooves are closed after pressing.

Figure 9:
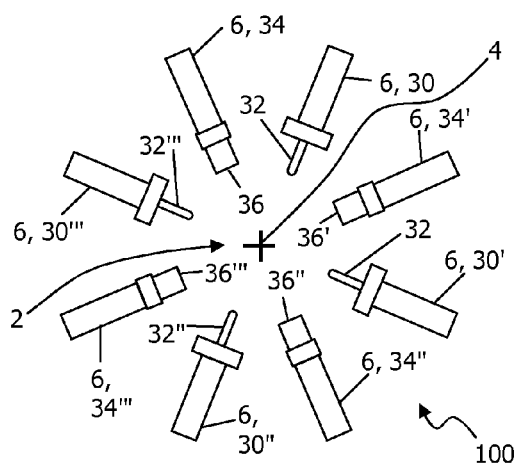
FIG. 9 shows in schematic form an arrangement of press jaws according to an embodiment of the invention, viewed along the press axis, where the jaws comprise alternately penetrating segments for the longitudinal groove and for the side grooves.

Another embodiment of a press apparatus 100 of the current invention is described in more detail below and exemplified by FIGS. 9 to 16. FIG. 9 shows the press jaws of an embodiment of press 100 according to the invention in open position. There are two groups of jaws 6, the first group 30, 30', 30", 30'" provided with PSLGs 32, 32', 32", 32'", the second group 34, 34', 34", 34'", provided with PSSGs 36, 36', 36", 36' facing the press opening 2. The first 30, 30', 30", 30'" and second group 34, 34', 34", 34'" of jaws alternate. The press jaws 6 are arranged in a star formation around the press axis 4. The PSLGs in profile are shown to have a greater maximum height (HL) compared with that of the PSSG (HS).

Figure 10:
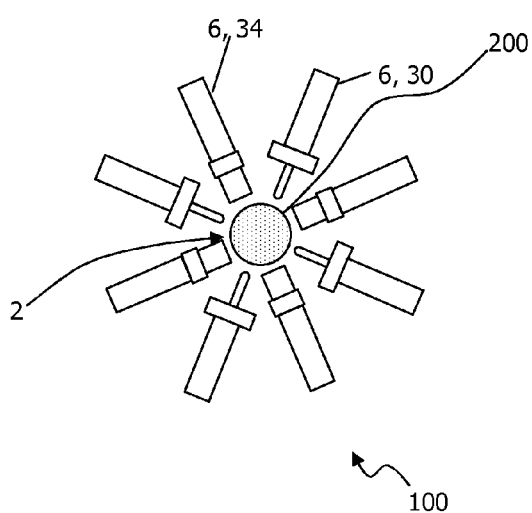
FIGS. 10 to 16 depict a pressing cycle, FIG. 10, tampon blank is inserted into a press opening.
Figure 11:
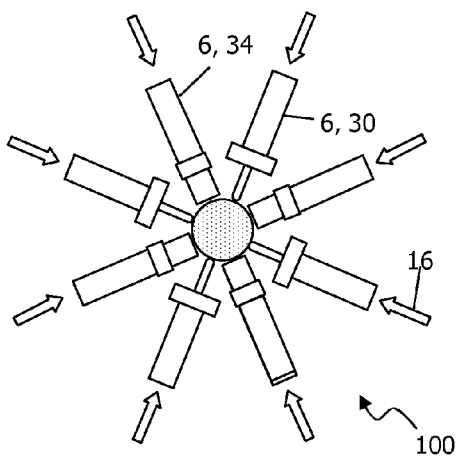
Figure 12:
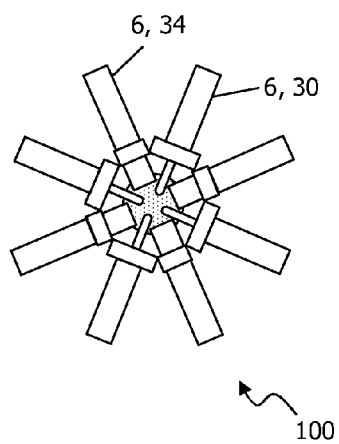
Figure 13:
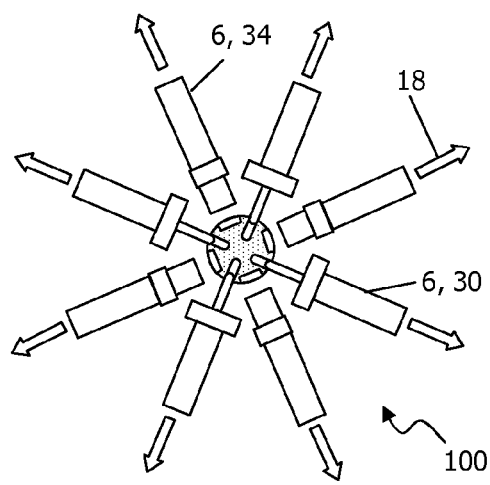
Figure 16:
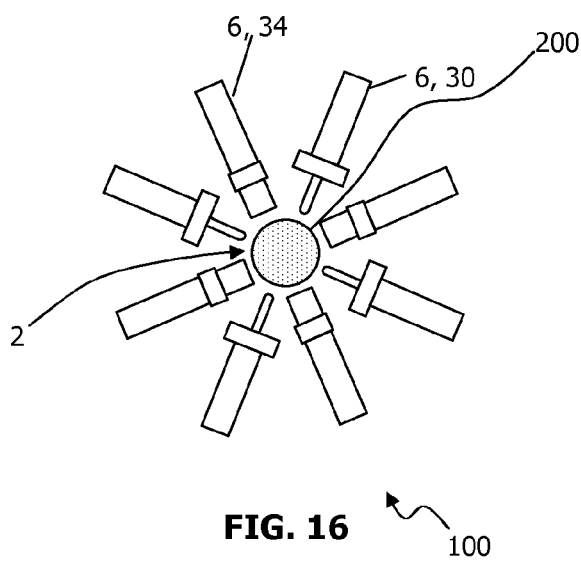

FIG. 10 shows the press 100 with a blank tampon 200 inserted in the press opening 2. In FIG. 11 the press jaws 6 synchronously advance 16 radially towards the press axis 4, penetrating and pressing the tampon blank 200 as depicted in FIG. 12. While FIG. 12 does not show the jaws supported on one another on their mutually opposite longitudinal sides in the closed position, this aspect is preferable and within the scope of the invention. In FIG. 13 the press jaws are retracted 18 to a holding position, to the extent that the PSSG are entirely withdrawn from the preform so produced, while the PSLG remain in contact with the longitudinal grooves. In that holding position, the preform 210 is ejected (FIG. 14) by means of a ram (not shown) that slidably propels the preform along the tips of the PSLG, parallel to the press axis 4 and out towards the other side of the press 100. It is noted that the grooves in the drawings have been enlarged for clarity; it is understood in practice, they are closed after pressing. The press jaws fully retract 20 (FIG. 15) by a sufficient distance to allow insertion of a new tampon blank 200 (FIG. 16).

By utilising a differential withdrawal of the PSLG compared with the PSSG in the holding position, advantageously, the tampon is suspended circumferentially with minimum contact with the press and is ejected in a slidable manner, guided by the longitudinal grooves. This results in the ribs and side grooves being untouched by the press during ejection, so maintaining their integrity and limiting exposure to contaminants. The tampon can be ejected at great speed. This compares with the art which must allow the tampon to fall to the floor of the press opening. The latter exposes the preform ribs potentially to contamination by the contact with the longitudinal sides of the opened jaw, and to damage by propulsion across a plurality of penetrating segments.

Figure 17:
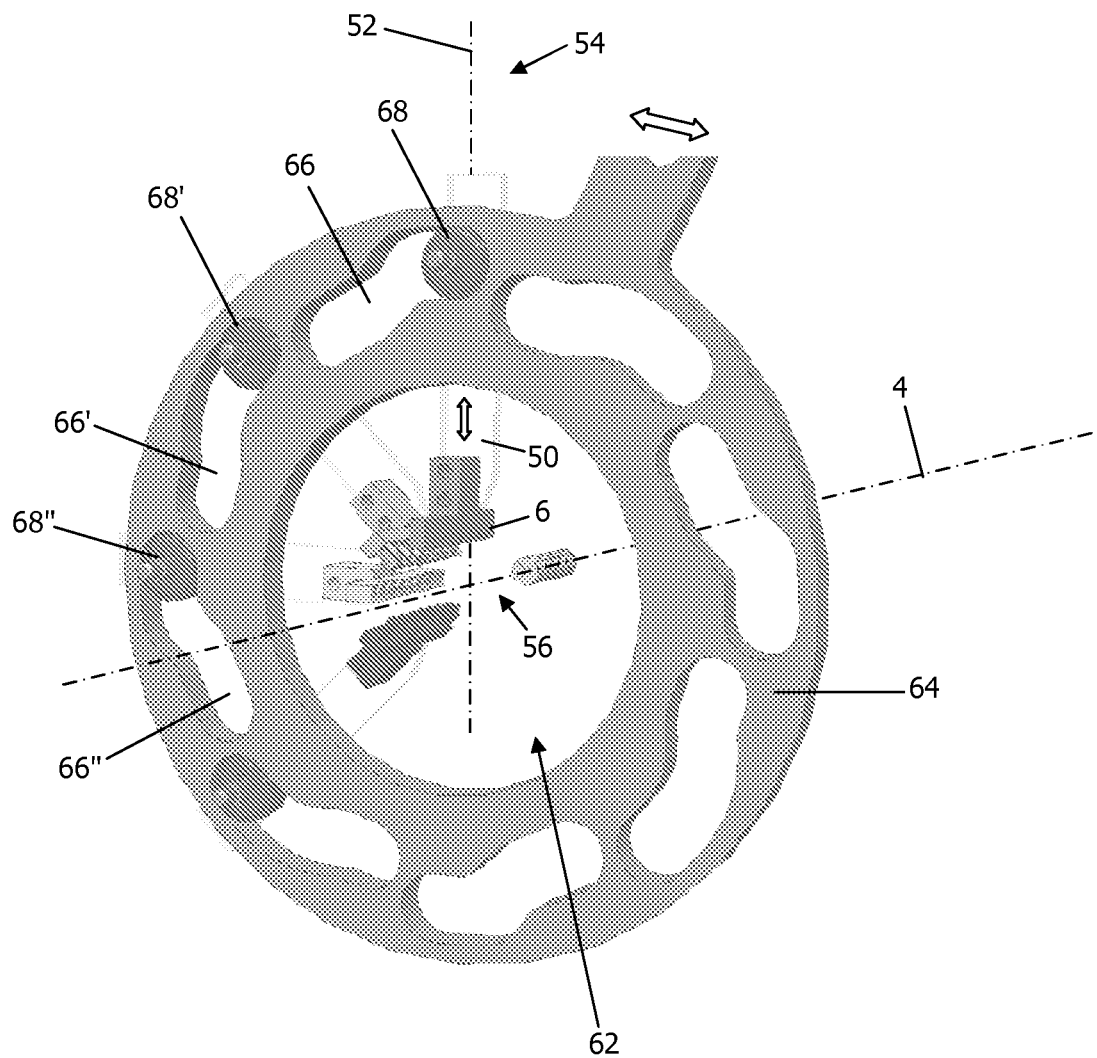
FIG. 17 shows a three dimensional representation of a mechanism for control movement of the press jaws.

According to one aspect of the invention, as shown in FIG. 17, each press jaw 6 is connected to a longitudinal transmission rod 50, aligned essentially radially to the press axis 4, or inclined to the radius centred on the press axis. The transmission rod has, at one longitudinal side, a proximal end 56 closer to the press axis 4 and, at the opposing longitudinal side, a distal end 54 directed away from the press axis 4. The press comprises eight jaws 6, each in rigid connection with the rod 50. The rods are configured for slidable linear displacement along an axis of movement 52 that is essentially radial to the press axis 4, or inclined to the radius. Linear force applied to the distal end 54 of the rod 50 is transmitted to the press jaw 6 which is linearly displaced accordingly. A rotatable annular plate 64 having essentially an annulus shape, disposed with a central part (opening) 62 and having a central axis in co-axial alignment with press axis 4 is provided with a plurality of discrete slots 66 on the plate 64, one slot for each rod, which slot engages with a roller 68 in revolute attachment to the distal end 54 of each rod 50. The roller 68 is in slidable connection with the slot 66. The opening 62 accommodates the press jaws 6. The axis of rotation of the roller 68 is perpendicular to the longitudinal axis of the rod 52 and is parallel with the press axis 4. The rotation of the annular plate 64 effects movement of the roller 68 along the axis of movement 52, and translation of the rod 50 towards or away from the press axis 4. The slot 66 is shaped to retract or advance press jaw 6 in the direction of the press axis 4 according to the angle of rotation of the annular plate 64 around its central axis. The circumferential path of the slot 66 is, at one extreme (preferably end) radially closer to the press axis 4 to obtain a closed press jaw 6, and at the other extreme (preferably end), radially further removed from the press axis 4 to obtain an open press jaw 6, the radial distance of the slot 66 path from the central axis transitioning gradually between the extremes. The holding position is maintained by pausing rotation of the annular plate 64 in the transition part of the slot 66. Rotation of the annular plate 64 around its central axis thereby controls advancement or retraction of the press jaws 6 simultaneously. A production cycle will generally imply consecutive clockwise and anticlockwise rotations of the annular plate 64, and pausing at the holding position during ejection.

The press jaws can preferably be heated and preferably each press jaw has its own temperature sensor. By heating the press jaws, it is possible to reduce the memory effect of modern, highly absorbent, greatly expanding fibrous materials, which occurs after the tampon has been finished. By means of the heated press jaws, and especially the heated pressing shoulders, the surface of the tampon is simultaneously smoothed during pressing and pushing out, and a qualitatively improved surface is produced in the preformed tampon even in tampon preforms of low weight, the stability of the tampon preform being preserved. The memory effect of the fibrous material becomes effective again when the fibrous material of the tampon is wetted with body fluid.

According to one aspect of the invention, the tips 15, 15' of the penetrating segments 11, 13 touch a fictive cylinder (PSFC) centred on the press axis when the jaws 6 are in the closed position, and the diameter of the PSFC is constant across the longitudinal axial length of the press. According to another aspect of the invention, the PSFC has a variable diameter across the longitudinal axial length of the press.

According to one aspect of the invention, the shoulders of the press jaws touch a fictive cylinder (SFC) centred on the press axis when the jaws 6 are in the closed position, and the diameter of the SFC is constant across the longitudinal length of the press. According to another aspect of the invention, the SFC has a variable diameter. The variation in SFC longitudinally may provide tampons having different profiles, for example, having a mushroom-shape, domed head, constricted, preferably conical withdrawal end, barrel shape, bullet shape etc.

The invention further concerns a method for manufacturing the tampon in particular for feminine hygiene having a longitudinal body in an essentially cylindrical shape. The tampon is divided into a number of longitudinal grooves that flank longitudinal ribs, and is provided with a plurality of side grooves that are spatially arranged and separated in the longitudinal direction, between, adjoining or crossing the longitudinal grooves. A strip of absorbent material having acceptable absorbency and modulus of elasticity properties that is capable of absorbing and/or retaining liquid, is wound up on itself to form an essentially cylindrical tampon blank that is subsequently pressed.

Absorbent fibrous material usable in the tampon produced to the invention may consist of any absorbent material having acceptable absorbency and modulus of elasticity properties that is capable of absorbing and/or retaining liquid. The absorbent structure can be manufactured in a wide variety of sizes and shapes and from a wide variety of liquid-absorbing materials. It is, of course, desirable to use absorbent materials having a minimum content of extraneous soluble materials since the product may be retained in the body for a considerable period of time. Retained soluble extraneous materials could cause a safety hazard if they are toxic, irritant, or sensitive. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibres; synthetic materials, such as polyester fibres, polyolefin fibres, absorbent foams, e.g. a flexible resilient polyurethane foam, absorbent sponges, super-absorbent polymers, absorbent gelling materials; formed fibres, such as capillary channel fibres and multi limbed fibres; synthetic fibres, or any equivalent material or combinations of materials, or mixtures of these.

In one embodiment, the essentially cylindrical blank is not surrounded by a covering, particularly when the blank tampon is made from cotton. In a preferred embodiment, the essentially cylindrical blank is at least partially surrounded by a covering. The covering is preferably not provided at the portion which will form the insertion end of the tampon. In order to improve the absorbing capacity and expansion capacity of the tampon, said covering is preferably a stretchable or elastic liquid-permeable covering.

The tampon blank is pressed with the pressing apparatus described above. In order to form the ribs and side grooves of the tampon, the method comprises compressing the tampon blank on its outer circumferential surface, forming longitudinal grooves, side grooves and a fibre core. Preferably, the fibre core has a higher degree of compression from which less compressed longitudinal ribs extend outward.

In detail, a preferably cylindrical tampon blank is introduced in the press apparatus described above. The tampon blank is radially compressed or compressed in a direction inclined to the radius by press jaws, such as those described above. If the penetrating segments and the pressing shoulders are fixed to separate press jaws, the tampon blank may be first pressed with the penetrating segments and subsequently with the pressing shoulders. Alternatively, the penetrating segments and the pressing shoulders may press the tampon blank simultaneously. The latter will obviously be the case when the penetrating segments and pressing shoulders are fixed to the same press jaws. In the press, the tampon blank is preferably compressed in a single pressing operation by the penetrating segments and pressing shoulders simultaneously.

The penetrating segments configured to provide longitudinal grooves (PSLG) will preferably press the tampon blank on strips of the circumferential surface which are narrower than the strips of the circumferential surface pressed by the pressing shoulders. Preferably also, the strips pressed by the penetrating segments have an equal length and width and the strips pressed by the pressing shoulders also have an equal length and width. In this way, ribs are formed, defined by longitudinal grooves on a solid fibre core.

The penetrating segments configured to provide side grooves (PSSG) press the tampon blank on the ribs, between, adjoining, or crossing the grooves. The pressing shoulders will press on the circumference of the so formed ribs and side grooves in order to obtain an essentially cylindrical form with a smaller diameter. The memory effect of the tampon blank maintains the shape of the compressed tampon form.

Figure 6:
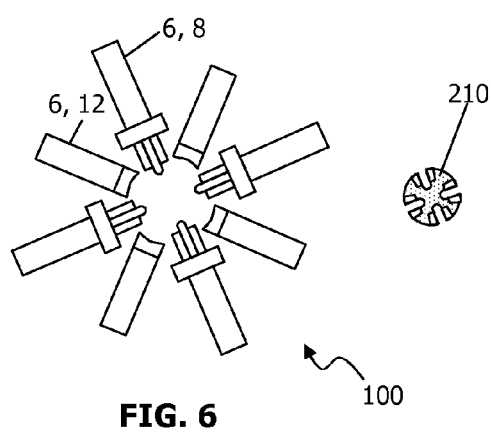
Figure 7:
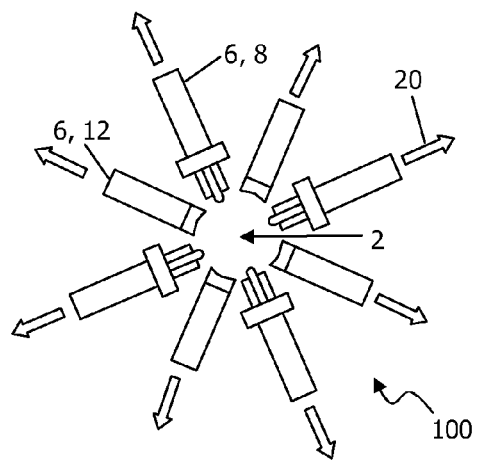
Figure 14:
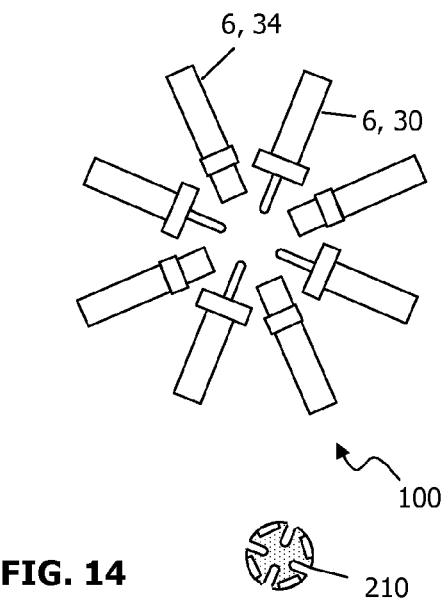
Figure 15:
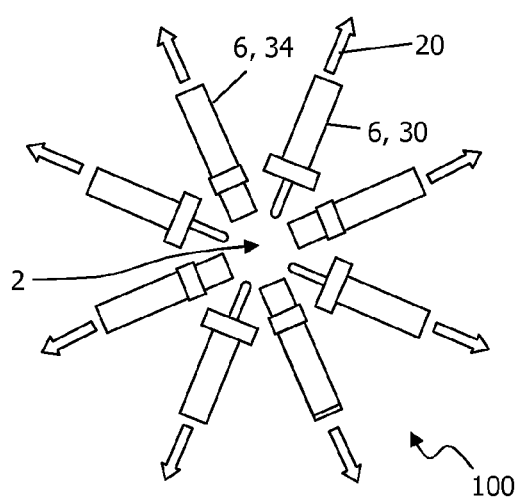

The tampon blank, having been pressed by the penetrating segments and pressing shoulders, forms a preform (pressed cylindrical blank) which is ejected from the press. Prior to ejection, the press jaws retract simultaneously to the extent that the PSSGs are fully withdrawn from the preform, while contact is maintained between the preform and the PSLGs. Thus, the preform becomes suspended in the partially closed jaws by the circumferential arrangement of PSLGs, but is free from contact with the PSSG. Accordingly, the preform is propelled longitudinally while in slidable contact only with the PSLGs. By invoking a slidable ejection along the PSLGs, the integrity of the preform is maintained, avoiding damage to its surface by otherwise protruding PSSGs in the ejection passage. Equally, ejection of the preform while the jaws are open fully would lead to damage as the space between two jaws into which the tampon is released provides only an obstructive and unhygienic passage for slidable ejection. An example of a preform formed by the press of the invention is schematically depicted in FIGS. 6 and 14.

One embodiment of the invention concerns a process for manufacturing a tampon having a longitudinal axis, comprising the steps:

a) inserting a cylindrical blank 200 of absorbing material in a press for manufacturing a tampon which presses absorbing material radially or inclined to the radius, which press comprises at least three press jaws 6 arranged in a star formation, whereby there is provided on a single or separate adjacent press jaws:

a penetrating segment, PSLG, configured to penetrate the absorbing material with a longitudinal groove, and penetrating segments, PSSG, configured to penetrate the absorbing material with a plurality of side grooves that are arranged in the longitudinal direction, b) pressing the tampon blank in the press jaws, such that:
the PSLG penetrates the cylindrical blank to form longitudinal ribs 12 defined by longitudinal grooves,
PSSG penetrate the cylindrical blank to form a plurality of side grooves that are arranged in the longitudinal direction, between, adjoining or crossing the longitudinal grooves,
so forming a preform,
c) moving the press jaws to a holding position between the closed position and open position, so that the preform can be removed, and
d) removing the pressed cylindrical blank from the press while the press jaws are maintained in the holding position.

Besides being arranged in the longitudinal direction, at least one, preferably each and every side groove may also be spatially separated from adjacent or other side grooves. As mentioned elsewhere, at least one, preferably each and every side groove may adjoin or cross adjacent longitudinal grooves. At least one, preferably each and every side groove may be in spatially separated from one or both adjacent longitudinal grooves. In step b) the press jaws 6 are moved (advanced) to a closed position to press the cylindrical blank 200 so forming a preform 210. The movement, towards the press axis, is preferably radial or may be inclined to the radius of the press axis. The cylindrical blank is, thus, pressed radially or may be pressed inclined to the radius of the press axis.

In step c), the press jaws 6 are moved (retracted) to a holding position between the closed position and open position, so that the preform can be removed axially, preferably without substantial obstruction. Preferably, the holding position is where the tips 15' of the PSSGs 11 are moved (retracted) to a greater distance from the press axis 4 compared with the tips 15 of the PSLGs, such that the PSSGs are withdrawn, preferably fully, from the preform, while contact is maintained between the preform longitudinal grooves and the PSLGs 13.

In step d) the preform is removed (ejected), preferably slidably, while the jaws (6) are in the holding position. In a subsequent step, the press jaws 6 are moved (retracted) to the open position for loading of another cylindrical blank. The sequence of steps may be repeated for a subsequent cylindrical blank.

The press used in the process may that as defined elsewhere herein.

Another embodiment of the invention is a tampon obtainable by a process of the invention.

This preform may be simultaneously subjected to final shaping downstream so forming a tampon. This final shaping includes a radial pressure being exerted on the total circumference of the preform. This radial pressure has the effect that the adjacent longitudinal ribs are pressed against one another, so that the longitudinal grooves are substantially closed and the circumferential surface of the tampon is substantially smooth and soft.

The tampon blank is, depending on the properties of the fibrous material used, in particular in the event of use being made of highly expansive fibres of irregular cross section with a strong memory effect, pressed at a temperature of the press jaws to the final shape of the tampon, in order to achieve the desired dimensional stability of the fibrous material by eliminating the memory effect of the fibres, which immediately becomes effective again on contact with bodily fluid and thus increases the expansion and absorption speed of the tampon with the least possible use of fibrous material.

It is apparent that there has been provided in accordance with the invention, a tampon that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

What is claimed is:

1. Press for manufacturing a tampon, comprising at least three press jaws arranged in a star around a central longitudinal press axis forming a press opening, whereby there is provided on a single or separate adjacent press jaws:
   a penetrating segment, PSLG, configured to penetrate the absorbing material with a longitudinal groove, and
   penetrating segments, PSSG, configured to penetrate the absorbing material with a plurality of side grooves that are arranged in the longitudinal direction,
wherein the press is configured to:
   a) load a cylindrical blank in the press opening,
   b) move the press jaws to a closed position to press the cylindrical blank so forming a preform,
   c) move the press jaws to a holding position between the closed position and open position, so that the preform can be removed,
   d) remove the preform while the jaws are in the holding position, and
   e) move the press jaws to the open position for loading of a subsequent cylindrical blank.

2. Press according to claim 1, wherein the press jaws are configured to move synchronously.

3. Press according to claim 1, wherein each PSSG is in the shape essentially of a chevron (v-shaped), straight-edged slot, undulating, star, cross, diamond, circular, oval, triangle, rectangle, pentagon, hexagon, septagon, octagon, nonagon, decagon, other polygon, or the like.

4. Press according to claim 1, wherein at least one PSSG is spatially separated from the PSLG when the press jaws are closed.

5. Press according to claim 1, wherein at least one PSSG is in connection with the PSLG when the press are closed.

6. Press according to claim 1, wherein the number of PSSGs disposed on a press jaw is between 3 and 7.

7. Press according to claim 1, wherein the maximum height, HL, of the PLSG from the base to the tip is greater than the maximum height, HS, of the PSSG from the base to the tip.

8. Press according to claim 1, wherein the press jaws further comprise one or more pressing shoulders for finish shaping of the preform.

9. Press according to claim 8, wherein during pressing, the pressing shoulders are configured to produce a preform having a mushroom-shape, domed head, constricted withdrawal end, conical withdrawal end, barrel shape, or a bullet shape.

10. Press according to claim 1, wherein:
   each press jaw is connected to a longitudinal transmission rod, aligned essentially radially to the press axis, or inclined to the radius centred on the press axis, said rod having a proximal end closer to the press axis and, at the opposing longitudinal side, a distal end directed away from the press axis, and is configured for slidable linear displacement along an axis of movement that is essentially radial to the press axis, or inclined to said radius
   the press further comprises a rotatable annular plate having a central axis in co-axial alignment with press axis and provided with a plurality of discrete slots on the plate, one slot for each rod, which slot engages with a roller in revolute attachment to the distal end of each rod, the roller being in slidable connection with the slot, the axis of rotation of the roller being perpendicular to the longitudinal axis of the rod and is parallel with the press axis, a ring is configured to rotate and thereby effect movement of the roller and translation the rod towards or away from the press axis along the axis of movement, and the slot shaped to retract or advance each press jaw in the direction of the press axis according to the angle of rotation of the annular plate around its central axis.

11. Press according to claim 1, wherein the press jaws in step b) are moved to a closed position in a direction essentially radial or inclined to the radius of the press axis.

12. Press according to claim 1, wherein the press jaws in step c) are moved to a holding position between the closed position and open position, in which the tips of the PSSGs are retracted to a greater distance from the press axis compared with the tips of the PSLGs, such that the PSSGs are fully withdrawn from the preform, while contact is maintained between the preform longitudinal grooves and at least one PSLG.

13. Press according to claim 1, wherein at least one side groove is spatially separated from adjacent side grooves.

14. Process for manufacturing a tampon having a longitudinal axis, comprising the steps:

inserting a cylindrical blank of absorbing material in a press for manufacturing a tampon which presses absorbing material radially, which press comprises at least three press jaws arranged in a star formation, whereby there is provided on a single or separate adjacent press jaws:

a penetrating segment, PSLG, configured to penetrate the absorbing material with a longitudinal groove, and penetrating segments, PSSG, configured to penetrate the absorbing material with a plurality of side grooves that are arranged in the longitudinal direction, at least one side groove being spatially separated from adjacent side grooves, pressing the tampon blank in the press jaws, such that:
the PSLG penetrates the cylindrical blank to form longitudinal ribs defined by longitudinal grooves,
PSSG penetrate the cylindrical blank to form a plurality of side grooves that are spatially arranged and separated in the longitudinal direction, between, adjoining or crossing the longitudinal grooves, so forming a preform, moving the press jaws to a holding position between the closed position and open position, so that the preform can be removed, removing the preform from the press while the press jaws are maintained in the holding position.

15. Process according to claim 14, wherein the press comprises at least three press jaws arranged in a star around a central longitudinal press axis forming a press opening, whereby there is provided on a single or separate adjacent press jaws:

the penetrating segment, PSLG, configured to penetrate the absorbing material with the longitudinal groove, and penetrating segments, PSSG, configured to penetrate the absorbing material with a plurality of side grooves that are arranged in the longitudinal direction, wherein the press is configured to:
a) load the cylindrical blank in the press opening,
b) move the press jaws to the closed position to press the cylindrical blank so forming the preform,
c) move the press jaws to the holding position between the closed position and open position, so that the preform can be removed,
d) remove the preform while the jaws are in the holding position, and
e) move the press jaws to the open position for loading of a subsequent cylindrical blank.

16. Tampon obtainable by a process according to claim 14.

* * * * *